US012569620B2

(12) United States Patent
Urszuy et al.

(10) Patent No.: US 12,569,620 B2
(45) Date of Patent: Mar. 10, 2026

(54) TOOL FOR SERVICING AN AUTO-INJECTOR

(71) Applicant: Birya Biotech, Inc., Baltimore, MD (US)

(72) Inventors: Tzvi Mordechai Urszuy, Baltimore, MD (US); John Hall, Baltimore, MD (US)

(73) Assignee: BIRYA BIOTECH, INC., Baltimore, MD (US)

( * ) Notice: Subject to any disclaimer, the term of this patent is extended or adjusted under 35 U.S.C. 154(b) by 1116 days.

(21) Appl. No.: 16/963,186

(22) PCT Filed: Jan. 18, 2019

(86) PCT No.: PCT/US2019/014353
§ 371 (c)(1),
(2) Date: Jul. 17, 2020

(87) PCT Pub. No.: WO2019/144048
PCT Pub. Date: Jul. 25, 2019

(65) Prior Publication Data
US 2021/0121631 A1 Apr. 29, 2021

Related U.S. Application Data

(60) Provisional application No. 62/619,236, filed on Jan. 19, 2018.

(51) Int. Cl.
*A61M 5/20* (2006.01)
*A61M 5/28* (2006.01)
(Continued)

(52) U.S. Cl.
CPC ............... *A61M 5/20* (2013.01); *A61M 5/28* (2013.01); *A61M 5/3205* (2013.01); *B25B 27/146* (2013.01); *A61M 2209/045* (2013.01)

(58) Field of Classification Search
CPC ........ A61M 5/20; A61M 5/28; A61M 5/3205; A61M 2209/045; B25B 27/146;
(Continued)

(56) References Cited

U.S. PATENT DOCUMENTS 807,334 A 12/1905 Swank
2,101,140 A 12/1937 Hege
(Continued)

FOREIGN PATENT DOCUMENTS

CN 204603701 U 9/2015
WO WO-2010/119622 A1 10/2010

OTHER PUBLICATIONS

International Search Report mailed May 23, 2019 in corresponding International Application No. PCT/US2019/014353, 4 pages.
(Continued)

*Primary Examiner* — Monica S Carter
*Assistant Examiner* — Caleb Andrew Holizna
(74) *Attorney, Agent, or Firm* — FOLEY & LARDNER LLP

(57) ABSTRACT

An apparatus and method are provided for opening auto-injectors for subsequent servicing and refilling with medicament. The apparatus opens and disassembles an auto-injector to gain access to its drug reservoir so that a replacement medicament may be applied. The apparatus provides for reassembling the auto-injector as a medical device for subsequent service.

5 Claims, 29 Drawing Sheets

(51) Int. Cl.
A61M 5/32     (2006.01)
B25B 27/14    (2006.01)

(58) Field of Classification Search
CPC ..... B25B 5/003; B25B 5/12; Y10T 29/53652;
Y10T 29/53657; Y10T 29/53683; Y10T
29/53796; Y10T 29/53896; Y10T
29/53909; Y10T 29/53961; Y10T
29/53978; Y10T 29/53974; Y10T
29/53987; Y10T 29/53983
USPC ......................................................... 29/244
See application file for complete search history.

(56) References Cited

U.S. PATENT DOCUMENTS

| | | | |
|---|---|---|---|
| 2,671,448 A | 3/1954 | Harnisch |
| 2,752,918 A | 7/1956 | Uytenbogaart |
| 2,832,339 A | 4/1958 | Sarnoff et al. |
| 3,066,670 A | 12/1962 | Stauffer |
| 3,136,313 A | 6/1964 | Enström et al. |
| 3,166,069 A | 1/1965 | Enstrom et al. |
| 3,563,098 A | 2/1971 | Gley |
| 3,882,863 A | 5/1975 | Sarnoff et al. |
| 4,031,893 A | 6/1977 | Kaplan et al. |
| 4,196,732 A | 4/1980 | Wardlaw |
| 4,258,713 A | 3/1981 | Wardlaw |
| 4,261,358 A | 4/1981 | Vargas et al. |
| 4,394,863 A | 7/1983 | Bartner |
| 4,447,231 A | 5/1984 | Bekkering |
| 4,484,910 A | 11/1984 | Sarnoff et al. |
| 4,516,967 A | 5/1985 | Kopfer |
| 4,518,384 A | 5/1985 | Tarello et al. |
| 4,573,971 A | 3/1986 | Kamstra |
| 4,578,064 A | 3/1986 | Sarnoff et al. |
| 4,624,393 A | 11/1986 | Lopez |
| 4,624,660 A | 11/1986 | Mijers et al. |
| 4,643,721 A | 2/1987 | Brunet |
| 4,678,461 A | 7/1987 | Mesa |
| 4,713,061 A | 12/1987 | Tarello et al. |
| 4,723,937 A | 2/1988 | Sarnoff et al. |
| 4,747,839 A | 5/1988 | Tarello et al. |
| 4,755,169 A | 7/1988 | Sarnoff et al. |
| 4,795,433 A | 1/1989 | Sarnoff |
| 4,820,286 A | 4/1989 | van der Wal |
| 4,822,340 A | 4/1989 | Kamstra |
| 4,950,246 A | 8/1990 | Muller |
| 4,968,302 A | 11/1990 | Schluster et al. |
| 4,983,164 A | 1/1991 | Hook et al. |
| 5,041,088 A | 8/1991 | Ritson et al. |
| 5,085,642 A | 2/1992 | Sarnoff et al. |
| 5,092,843 A | 3/1992 | Monroe et al. |
| 5,102,393 A | 4/1992 | Sarnoff et al. |
| 5,137,516 A | 8/1992 | Rand et al. |
| 5,254,096 A | 10/1993 | Rondelet et al. |
| 5,295,965 A | 3/1994 | Wilmot |
| 5,298,023 A | 3/1994 | Haber et al. |
| 5,334,144 A | 8/1994 | Alchas et al. |
| 5,354,286 A | 10/1994 | Mesa et al. |
| 5,391,151 A | 2/1995 | Wilmot |
| 5,425,715 A | 6/1995 | Dalling et al. |
| 5,478,316 A | 12/1995 | Bitdinger et al. |
| 5,514,097 A | 5/1996 | Knauer |
| 5,527,287 A | 6/1996 | Miskinyar |
| 5,535,746 A | 7/1996 | Hoover et al. |
| 5,540,664 A | 7/1996 | Wyrick |
| 5,569,190 A | 10/1996 | D'Antonio |
| 5,569,192 A | 10/1996 | van der Wal |
| 5,588,966 A * | 12/1996 | Atsumi ............... A61M 5/3205 |
| | | 604/110 |
| 5,620,421 A | 4/1997 | Schmitz |
| 5,658,259 A | 8/1997 | Pearson et al. |
| 5,665,071 A | 9/1997 | Wyrick |
| 5,690,618 A | 11/1997 | Smith et al. |
| 5,695,472 A | 12/1997 | Wyrick |

| | | | |
|---|---|---|---|
| 5,709,662 A | 1/1998 | Olive et al. |
| 5,713,866 A | 2/1998 | Wilmot |
| 5,779,677 A | 7/1998 | Frezza |
| 5,833,669 A | 11/1998 | Wyrick |
| 5,865,795 A | 2/1999 | Schiff et al. |
| 5,865,804 A | 2/1999 | Bachynsky |
| 5,957,886 A | 9/1999 | Weston |
| 5,957,897 A | 9/1999 | Jeffrey |
| 5,984,900 A | 11/1999 | Mikkelsen |
| 6,063,059 A | 5/2000 | Kriesel |
| 6,077,247 A | 6/2000 | Marshall et al. |
| 6,099,503 A | 8/2000 | Stradella |
| 6,132,414 A | 10/2000 | Herbst et al. |
| 6,135,979 A | 10/2000 | Weston |
| 6,203,530 B1 | 3/2001 | Stewart, Sr. |
| 6,221,044 B1 | 4/2001 | Greco |
| 6,270,479 B1 | 8/2001 | Bergens et al. |
| 6,572,581 B1 | 6/2003 | Landau |
| 6,607,508 B2 | 8/2003 | Knauer |
| 6,641,561 B1 | 11/2003 | Hill et al. |
| 6,656,150 B2 | 12/2003 | Hill et al. |
| 6,656,163 B1 | 12/2003 | Marshall et al. |
| 6,702,778 B2 | 3/2004 | Hill et al. |
| 6,726,661 B2 | 4/2004 | Munk et al. |
| 6,770,052 B2 | 8/2004 | Hill et al. |
| 6,793,646 B1 | 9/2004 | Giambattista et al. |
| 6,893,420 B2 | 5/2005 | Arnisolle |
| 6,899,698 B2 | 5/2005 | Sams |
| 6,913,591 B2 | 7/2005 | Itoh et al. |
| 6,953,445 B2 | 10/2005 | Wilmot et al. |
| 7,011,649 B2 | 3/2006 | De La Serna et al. |
| 7,044,125 B2 | 5/2006 | Vedrine et al. |
| 7,097,634 B2 | 8/2006 | Gilbert |
| 7,128,728 B2 | 10/2006 | Kirchhofer et al. |
| 7,297,136 B2 | 11/2007 | Wyrick |
| 7,381,201 B2 | 6/2008 | Gilbert et al. |
| 7,416,540 B2 | 8/2008 | Edwards et al. |
| 7,488,308 B2 | 2/2009 | Lesch, Jr. |
| 7,500,963 B2 | 3/2009 | Westbye et al. |
| 7,517,334 B2 | 4/2009 | Jacobs et al. |
| 7,544,188 B2 | 6/2009 | Edwards et al. |
| 7,544,189 B2 | 6/2009 | Griffiths |
| 7,553,293 B2 | 6/2009 | Jensen et al. |
| 7,566,322 B2 | 7/2009 | Brand et al. |
| 7,569,035 B1 | 8/2009 | Wilmot et al. |
| 7,611,491 B2 | 11/2009 | Pickhard |
| 7,635,348 B2 | 12/2009 | Raven et al. |
| 7,635,350 B2 | 12/2009 | Scherer |
| 7,635,356 B2 | 12/2009 | Stamp |
| 7,645,265 B2 | 1/2010 | Stamp |
| 7,648,482 B2 | 1/2010 | Edwards et al. |
| 7,648,483 B2 | 1/2010 | Edwards et al. |
| 7,658,724 B2 | 2/2010 | Rubin et al. |
| 7,678,072 B2 | 3/2010 | Weber |
| 7,678,073 B2 | 3/2010 | Griffiths et al. |
| 7,708,719 B2 | 5/2010 | Wilmot et al. |
| 7,717,877 B2 | 5/2010 | Lavi et al. |
| 7,736,333 B2 | 6/2010 | Gillespie |
| 7,740,618 B2 | 6/2010 | Markussen |
| 7,749,192 B2 | 7/2010 | Hoffman |
| 7,758,548 B2 | 7/2010 | Gillespie et al. |
| 7,811,254 B2 | 10/2010 | Wilmot et al. |
| 7,815,598 B2 | 10/2010 | Hommann et al. |
| 7,909,796 B2 | 3/2011 | Weber |
| 7,918,824 B2 | 4/2011 | Bishop et al. |
| 7,955,304 B2 | 6/2011 | Guillermo |
| 7,959,600 B2 | 6/2011 | Chang et al. |
| 7,976,499 B2 | 7/2011 | Grunhut et al. |
| 7,976,514 B2 | 7/2011 | Abry et al. |
| 7,988,675 B2 | 8/2011 | Gillespie, III et al. |
| 8,038,649 B2 | 10/2011 | Kronestedt |
| 8,048,035 B2 | 11/2011 | Mesa et al. |
| 8,048,037 B2 | 11/2011 | Kohlbrenner et al. |
| 8,057,427 B2 | 11/2011 | Griffiths et al. |
| 8,070,713 B2 | 12/2011 | Matusch |
| 8,075,515 B2 | 12/2011 | Matusch |
| 8,092,419 B2 | 1/2012 | Matusch |
| 8,105,271 B2 | 1/2012 | Matusch |
| 8,128,603 B2 | 3/2012 | Langley et al. |

(56)    References Cited

U.S. PATENT DOCUMENTS

| | | | |
|---|---|---|---|
| 8,167,840 B2 | 5/2012 | Matusch |
| 8,231,573 B2 | 7/2012 | Edwards et al. |
| 8,262,604 B2 | 9/2012 | Asmussen et al. |
| 8,277,412 B2 | 10/2012 | Kronestedt |
| 8,277,414 B2 | 10/2012 | Barrow-Williams et al. |
| 8,287,490 B2 | 10/2012 | Asmussen et al. |
| 8,308,695 B2 | 11/2012 | Laiosa |
| 8,308,697 B2 | 11/2012 | Stamp et al. |
| 8,313,465 B2 | 11/2012 | Harrison |
| 8,328,738 B2 | 12/2012 | Frankhouser et al. |
| 8,357,125 B2 | 1/2013 | Grunhut et al. |
| 8,366,682 B2 | 2/2013 | Wyrick |
| 8,372,035 B2 | 2/2013 | Matusch |
| 8,377,008 B2 | 2/2013 | Abry et al. |
| 8,409,138 B2 | 4/2013 | James et al. |
| 8,480,631 B2 | 7/2013 | Wotton et al. |
| 8,491,530 B2 | 7/2013 | Maritan |
| 8,500,693 B2 | 8/2013 | Maritan |
| 8,556,866 B2 | 10/2013 | Krulevitch et al. |
| 8,560,271 B2 | 10/2013 | Koehler et al. |
| 8,568,359 B2 | 10/2013 | Carrel et al. |
| 8,632,504 B2 | 1/2014 | Young |
| 8,632,507 B2 | 1/2014 | Bartha |
| 8,632,509 B2 | 1/2014 | Moller et al. |
| 8,641,668 B2 | 2/2014 | Matusch |
| 8,647,299 B2 | 2/2014 | Stamp |
| 8,647,303 B2 | 2/2014 | Cowe |
| 8,647,306 B2 | 2/2014 | Schwirtz et al. |
| 8,652,100 B1 | 2/2014 | Cowe |
| 8,668,670 B2 | 3/2014 | Bicknell et al. |
| 8,672,898 B2 | 3/2014 | Enggaard |
| 8,672,901 B2 | 3/2014 | Bollenbach et al. |
| 8,679,055 B2 | 3/2014 | Ishikawa et al. |
| 8,684,969 B2 | 4/2014 | Moller et al. |
| 8,690,836 B2 | 4/2014 | Mathews et al. |
| 8,696,618 B2 | 4/2014 | Kramer et al. |
| 8,708,973 B2 | 4/2014 | Holmqvist |
| 8,708,975 B2 | 4/2014 | Heald |
| 8,734,393 B2 | 5/2014 | Cleathero |
| 8,758,301 B2 | 6/2014 | Shang et al. |
| 8,808,244 B2 | 8/2014 | Adlon et al. |
| 8,834,419 B2 | 9/2014 | Jennings |
| 8,834,454 B2 | 9/2014 | Genosar et al. |
| 8,864,718 B2 | 10/2014 | Karlsen et al. |
| 8,876,768 B2 | 11/2014 | Hourmand et al. |
| 8,876,782 B2 | 11/2014 | Veasey et al. |
| 8,894,619 B2 | 11/2014 | Stefanski |
| 8,900,197 B2 | 12/2014 | Crow |
| 8,911,402 B2 | 12/2014 | Veasey et al. |
| 8,911,410 B2 | 12/2014 | Ekman et al. |
| 8,915,886 B2 | 12/2014 | Cowe |
| 8,920,367 B2 | 12/2014 | Edwards et al. |
| 8,920,374 B2 | 12/2014 | Bokelman et al. |
| 8,922,367 B2 | 12/2014 | Denny et al. |
| 8,939,934 B2 | 1/2015 | Brereton et al. |
| 8,939,943 B2 | 1/2015 | Edwards et al. |
| 8,968,236 B2 | 3/2015 | Jennings et al. |
| 8,992,484 B2 | 3/2015 | Radmer et al. |
| 8,992,487 B2 | 3/2015 | Eich et al. |
| 9,011,387 B2 | 4/2015 | Ekman et al. |
| 9,017,293 B2 | 4/2015 | Edhouse et al. |
| 9,022,982 B2 | 5/2015 | Karlsson et al. |
| 9,028,453 B2 | 5/2015 | Jennings |
| 9,072,838 B2 | 7/2015 | Hogdahl |
| 9,072,839 B2 | 7/2015 | Kouyoumijian et al. |
| 9,078,983 B2 | 7/2015 | Herr |
| 9,084,849 B2 | 7/2015 | Edwards et al. |
| 9,089,652 B2 | 7/2015 | Nzike et al. |
| 9,125,986 B2 | 9/2015 | Holmqvist |
| 9,132,239 B2 | 9/2015 | Moller et al. |
| 9,132,241 B2 | 9/2015 | Guillermo |
| 9,144,649 B2 | 9/2015 | Plumptre |
| 9,155,836 B2 | 10/2015 | Hommann et al. |
| 9,180,244 B2 | 11/2015 | Anderson et al. |
| 9,180,258 B2 | 11/2015 | Kemp et al. |
| 9,192,729 B2 | 11/2015 | Iwase et al. |
| 9,205,196 B2 | 12/2015 | Harms et al. |
| 9,205,199 B2 | 12/2015 | Kemp et al. |
| 9,216,251 B2 | 12/2015 | Daniel |
| 9,220,842 B2 | 12/2015 | Grunhut |
| 9,220,847 B2 | 12/2015 | Holmqvist et al. |
| 9,227,016 B2 | 1/2016 | Ekman et al. |
| 9,227,017 B2 | 1/2016 | Buchine et al. |
| 9,233,209 B2 | 1/2016 | Markussen et al. |
| 9,233,215 B2 | 1/2016 | Hourmand et al. |
| 9,242,045 B2 | 1/2016 | Burnell et al. |
| 9,242,053 B2 | 1/2016 | Wozencroft |
| 9,248,245 B2 | 2/2016 | Ekman et al. |
| 9,272,098 B2 | 3/2016 | Hourmand et al. |
| 9,278,182 B2 | 3/2016 | Edwards et al. |
| 9,283,326 B2 | 3/2016 | Kemp et al. |
| 9,283,327 B2 | 3/2016 | Hourmand et al. |
| 9,320,855 B2 | 4/2016 | Holmqvist et al. |
| 9,327,082 B2 | 5/2016 | Kouyoumjian et al. |
| 9,333,304 B2 | 5/2016 | Brereton et al. |
| 9,345,831 B2 | 5/2016 | Raday et al. |
| 9,352,089 B2 | 5/2016 | Hourmand et al. |
| 9,352,090 B2 | 5/2016 | Brereton et al. |
| 9,364,611 B2 | 6/2016 | Kramer et al. |
| 9,402,957 B2 | 8/2016 | Adams et al. |
| 9,408,972 B2 | 8/2016 | Cappello et al. |
| 9,415,176 B1 | 8/2016 | Benson et al. |
| 9,421,337 B2 | 8/2016 | Kemp et al. |
| 9,427,527 B2 | 8/2016 | Dasbach et al. |
| 9,427,529 B2 | 8/2016 | Cabiri |
| 9,427,531 B2 | 8/2016 | Hourmand et al. |
| 9,440,026 B2 | 9/2016 | Wozencroft |
| 9,440,030 B2 | 9/2016 | Holmqvist |
| 9,446,195 B2 | 9/2016 | Kramer et al. |
| 9,457,149 B2 | 10/2016 | Kemp et al. |
| 9,468,719 B2 | 10/2016 | Muller-Pathle et al. |
| 9,468,720 B2 | 10/2016 | Mudd et al. |
| 9,474,866 B2 | 10/2016 | Hourmand et al. |
| 9,486,583 B2 | 11/2016 | Lannan et al. |
| 9,511,194 B2 | 12/2016 | Hourmand et al. |
| 9,526,837 B2 | 12/2016 | Carrel et al. |
| 9,539,392 B2 | 1/2017 | Jennings et al. |
| 9,539,393 B2 | 1/2017 | Johannesson et al. |
| 9,561,328 B2 | 2/2017 | Shang et al. |
| 9,572,937 B2 | 2/2017 | Ekman et al. |
| 9,579,453 B1 | 2/2017 | Brasington |
| 9,592,340 B2 | 3/2017 | Hourmand et al. |
| 9,616,181 B2 | 4/2017 | Kemp et al. |
| 9,616,183 B2 | 4/2017 | Wozencroft |
| 9,623,183 B2 | 4/2017 | Jennings et al. |
| 9,623,188 B2 | 4/2017 | Nielsen et al. |
| 9,636,460 B1 | 5/2017 | Jaeger et al. |
| 9,656,021 B2 | 5/2017 | Brereton et al. |
| 9,656,025 B2 | 5/2017 | Bostrom et al. |
| 9,675,754 B2 | 6/2017 | Desalvo et al. |
| 9,675,757 B2 | 6/2017 | Harrison |
| 9,682,194 B2 | 6/2017 | Jennings et al. |
| 9,687,616 B2 | 6/2017 | Cleathero |
| 9,707,344 B2 | 7/2017 | Cowe |
| 9,707,356 B2 | 7/2017 | Hourmand et al. |
| 9,707,357 B2 | 7/2017 | Fabien et al. |
| 9,731,084 B2 | 8/2017 | Pesach et al. |
| 9,737,663 B2 | 8/2017 | Jennings et al. |
| 9,737,668 B2 | 8/2017 | Holmqvist |
| 9,744,302 B2 | 8/2017 | Travanty |
| 9,750,885 B2 | 9/2017 | Weaver et al. |
| 9,757,513 B2 | 9/2017 | Mcloughlin et al. |
| 9,757,521 B2 | 9/2017 | Mcloughlin et al. |
| 9,757,523 B2 | 9/2017 | Macdonald et al. |
| 9,757,524 B2 | 9/2017 | Mcloughlin et al. |
| 9,770,558 B2 | 9/2017 | Burnell et al. |
| 9,775,948 B2 | 10/2017 | Bechmann et al. |
| 9,789,253 B2 | 10/2017 | Fabien et al. |
| 9,789,254 B2 | 10/2017 | Mcloughlin et al. |
| 9,789,255 B2 | 10/2017 | Brereton et al. |
| 9,802,003 B2 | 10/2017 | Harms et al. |
| 9,808,577 B2 | 11/2017 | Nagar et al. |
| 9,814,836 B2 | 11/2017 | Cowe |
| 9,814,839 B2 | 11/2017 | Eaton |

(56) References Cited

U.S. PATENT DOCUMENTS

| | | | |
|---|---|---|---|
| 9,821,115 B2 | 11/2017 | Wozencroft | |
| 9,821,118 B2 | 11/2017 | Adlon et al. | |
| 9,827,381 B2 | 11/2017 | Hourmand et al. | |
| 9,827,408 B2 | 11/2017 | Da Ros et al. | |
| 9,833,574 B2 | 12/2017 | Melander et al. | |
| 9,833,578 B2 | 12/2017 | Elmen | |
| 9,833,579 B2 | 12/2017 | Pedersen et al. | |
| 9,839,489 B2 | 12/2017 | Schaffer et al. | |
| 9,849,242 B2 | 12/2017 | Henley et al. | |
| 9,855,388 B2 | 1/2018 | Boyd et al. | |
| 9,861,749 B2 | 1/2018 | Nzike | |
| 9,867,940 B2 | 1/2018 | Holmqvist et al. | |
| 9,867,941 B2 | 1/2018 | Mcloughlin et al. | |
| 9,867,942 B2 | 1/2018 | Alexandersson | |
| 9,867,949 B2 | 1/2018 | Sund et al. | |
| 9,872,961 B2 | 1/2018 | Fourt et al. | |
| 9,895,492 B2 | 2/2018 | Fabien et al. | |
| 9,895,495 B2 | 2/2018 | Stefanski | |
| 9,907,911 B2 | 3/2018 | Constantineau et al. | |
| 9,919,107 B2 | 3/2018 | Imai et al. | |
| 9,919,109 B2 | 3/2018 | Arinobe et al. | |
| 9,925,344 B2 | 3/2018 | Brereton et al. | |
| 9,931,471 B2 | 4/2018 | Ekman et al. | |
| 9,950,121 B2 | 4/2018 | Banik | |
| 9,956,345 B2 | 5/2018 | Anderson et al. | |
| 9,956,353 B2 | 5/2018 | Rao et al. | |
| 9,956,354 B2 | 5/2018 | Park et al. | |
| 9,962,490 B2 | 5/2018 | Karlsson et al. | |
| 9,962,496 B2 | 5/2018 | Vogt et al. | |
| 9,981,086 B2 | 5/2018 | Cowe et al. | |
| 9,981,087 B2 | 5/2018 | Shang et al. | |
| 9,993,226 B2 | 6/2018 | Denny | |
| 9,999,734 B2 | 6/2018 | Cowe | |
| 2003/0105430 A1 | 6/2003 | Lavi et al. | |
| 2003/0229308 A1 | 12/2003 | Tsals et al. | |
| 2004/0039337 A1 | 2/2004 | Letzing | |
| 2004/0158195 A1 | 8/2004 | Sibert et al. | |
| 2005/0165349 A1 | 7/2005 | Stamp | |
| 2005/0222539 A1 | 10/2005 | Gonzales et al. | |
| 2005/0273054 A1 | 12/2005 | Asch | |
| 2006/0100588 A1 | 5/2006 | Brunnberg et al. | |
| 2006/0189938 A1 | 8/2006 | Hommann et al. | |
| 2006/0224124 A1 | 10/2006 | Scherer | |
| 2006/0270984 A1 | 11/2006 | Hommann | |
| 2006/0270985 A1 | 11/2006 | Hommann et al. | |
| 2006/0287630 A1 | 12/2006 | Hommann | |
| 2007/0027430 A1 | 2/2007 | Hommann | |
| 2007/0100288 A1 | 5/2007 | Bozeman et al. | |
| 2007/0135756 A1 | 6/2007 | Kohlbrenner et al. | |
| 2007/0167920 A1 | 7/2007 | Hommann | |
| 2007/0219498 A1 | 9/2007 | Malone et al. | |
| 2007/0265568 A1 | 11/2007 | Tsals et al. | |
| 2007/0293582 A1 | 12/2007 | Hill | |
| 2008/0262443 A1 | 10/2008 | Hommann | |
| 2008/0289984 A1 | 11/2008 | Raven et al. | |
| 2009/0005737 A1 | 1/2009 | Chun | |
| 2009/0018505 A1 | 1/2009 | Arguedas et al. | |
| 2009/0082753 A1 | 3/2009 | Dutcher et al. | |
| 2010/0036319 A1 | 2/2010 | Drake et al. | |
| 2010/0114038 A1 | 5/2010 | Sams | |
| 2011/0092906 A1 | 4/2011 | Bottger et al. | |
| 2011/0226646 A1 | 9/2011 | Wyrick | |
| 2011/0270161 A1 | 11/2011 | Harrison et al. | |
| 2011/0306938 A1 | 12/2011 | Cleathero | |
| 2012/0046609 A1* | 2/2012 | Mesa | A61M 5/5086 604/111 |
| 2012/0123387 A1 | 5/2012 | Gonzalez et al. | |
| 2012/0132201 A1 | 5/2012 | Pommereau | |
| 2012/0197195 A1 | 8/2012 | Basso et al. | |
| 2012/0209200 A1 | 8/2012 | Jones et al. | |
| 2012/0233834 A1 | 9/2012 | Szechinski et al. | |
| 2012/0253314 A1 | 10/2012 | Harish et al. | |
| 2012/0302992 A1 | 11/2012 | Brooks, Jr. et al. | |
| 2012/0310172 A1 | 12/2012 | Macdonald et al. | |
| 2013/0144220 A1 | 6/2013 | Cleathero et al. | |
| 2013/0150804 A1* | 6/2013 | Bianco | A61M 5/3276 604/241 |
| 2013/0245545 A1 | 9/2013 | Arnold et al. | |
| 2013/0274671 A1 | 10/2013 | Jennings et al. | |
| 2013/0274677 A1 | 10/2013 | Ekman et al. | |
| 2013/0296807 A1 | 11/2013 | Lintern et al. | |
| 2013/0310753 A1 | 11/2013 | Cabiri | |
| 2013/0317480 A1 | 11/2013 | Reber et al. | |
| 2013/0338593 A1 | 12/2013 | Wozencroft | |
| 2014/0005596 A1 | 1/2014 | Schuster | |
| 2014/0008366 A1 | 1/2014 | Genosar | |
| 2014/0010727 A1 | 1/2014 | Jugl et al. | |
| 2014/0046259 A1 | 2/2014 | Reber et al. | |
| 2014/0214001 A1 | 7/2014 | Mortazavi | |
| 2014/0236097 A1 | 8/2014 | Jugl et al. | |
| 2014/0276583 A1 | 9/2014 | Chen et al. | |
| 2014/0296824 A1 | 10/2014 | Edwards et al. | |
| 2014/0330243 A1 | 11/2014 | Kietzmann et al. | |
| 2014/0364812 A1 | 12/2014 | Lumme et al. | |
| 2014/0378911 A1 | 12/2014 | Dolk et al. | |
| 2015/0007425 A1* | 1/2015 | Dasbach | A61M 5/3205 29/281.1 |
| 2015/0011976 A1 | 1/2015 | Vouillamoz et al. | |
| 2015/0073383 A1 | 3/2015 | Wilmot et al. | |
| 2015/0088077 A1 | 3/2015 | Kemp et al. | |
| 2015/0119809 A1 | 4/2015 | Lööf | |
| 2015/0157803 A1 | 6/2015 | Radmer et al. | |
| 2015/0174324 A1 | 6/2015 | Wurmbauer et al. | |
| 2015/0174325 A1 | 6/2015 | Young et al. | |
| 2015/0174331 A1 | 6/2015 | Young et al. | |
| 2015/0202366 A1 | 7/2015 | Henderson et al. | |
| 2015/0202367 A1 | 7/2015 | Plaschkes et al. | |
| 2015/0209517 A1 | 7/2015 | Brunnberg et al. | |
| 2015/0217057 A1 | 8/2015 | Högdahl | |
| 2015/0231334 A1 | 8/2015 | Buchine et al. | |
| 2015/0258284 A1 | 9/2015 | Fenster et al. | |
| 2015/0273162 A1 | 10/2015 | Holmqvist | |
| 2015/0283323 A1 | 10/2015 | Young et al. | |
| 2015/0297833 A1 | 10/2015 | Henderson et al. | |
| 2015/0359978 A1 | 12/2015 | Egerström et al. | |
| 2015/0374925 A1 | 12/2015 | Standley et al. | |
| 2016/0008542 A1 | 1/2016 | Hirschel et al. | |
| 2016/0008544 A1 | 1/2016 | Molson et al. | |
| 2016/0015896 A1* | 1/2016 | Cowe | A61M 5/31571 604/198 |
| 2016/0015897 A1 | 1/2016 | Swanson et al. | |
| 2016/0022914 A1 | 1/2016 | Mounce et al. | |
| 2016/0038677 A1 | 2/2016 | Kiilerich | |
| 2016/0051494 A1 | 2/2016 | Gulfo | |
| 2016/0074584 A1 | 3/2016 | Carmel et al. | |
| 2016/0089498 A1 | 3/2016 | Daniel | |
| 2016/0089500 A1 | 3/2016 | Soerensen | |
| 2016/0106921 A1 | 4/2016 | Fraunhofer et al. | |
| 2016/0106924 A1 | 4/2016 | Bitar et al. | |
| 2016/0129201 A1 | 5/2016 | Jennings et al. | |
| 2016/0144117 A1 | 5/2016 | Chun | |
| 2016/0144131 A1 | 5/2016 | Schwirtz et al. | |
| 2016/0144135 A1 | 5/2016 | Taal et al. | |
| 2016/0151586 A1 | 6/2016 | Kemp | |
| 2016/0175524 A1 | 6/2016 | Henderson et al. | |
| 2016/0175525 A1 | 6/2016 | Oakley et al. | |
| 2016/0193413 A1 | 7/2016 | Gabrielsson | |
| 2016/0199588 A1 | 7/2016 | Kemp | |
| 2016/0213850 A1 | 7/2016 | Lööf et al. | |
| 2016/0213858 A1 | 7/2016 | Högdahl | |
| 2016/0220760 A1 | 8/2016 | Bilton et al. | |
| 2016/0220761 A1 | 8/2016 | Shetty et al. | |
| 2016/0220765 A1 | 8/2016 | Julian et al. | |
| 2016/0250162 A1 | 9/2016 | Miller | |
| 2016/0250418 A1 | 9/2016 | Olson | |
| 2016/0250419 A1 | 9/2016 | Griffiths et al. | |
| 2016/0263323 A1 | 9/2016 | Koppelman et al. | |
| 2016/0263325 A1 | 9/2016 | Huthmacher et al. | |
| 2016/0271329 A1 | 9/2016 | Park | |
| 2016/0287788 A1 | 10/2016 | Tremblay et al. | |
| 2016/0287812 A1 | 10/2016 | Nielsen et al. | |
| 2016/0303323 A1 | 10/2016 | Saussaye et al. | |
| 2016/0303327 A1 | 10/2016 | Moren | |
| 2016/0303330 A1 | 10/2016 | Holmqvist | |

(56) References Cited

U.S. PATENT DOCUMENTS

| | | |
|---|---|---|
| 2016/0310674 A1 | 10/2016 | Tornsten et al. |
| 2016/0317745 A1 | 11/2016 | Kjeldsen et al. |
| 2016/0331900 A1 | 11/2016 | Wei |
| 2016/0367763 A1 | 12/2016 | Tschirren et al. |
| 2016/0375195 A1 | 12/2016 | Fabien |
| 2016/0375196 A1 | 12/2016 | Wilmot et al. |
| 2017/0007764 A1 | 1/2017 | Saussaye |
| 2017/0035972 A1 | 2/2017 | Wilmot et al. |
| 2017/0049965 A1 | 2/2017 | Baker et al. |
| 2017/0049969 A1 | 2/2017 | Dunne et al. |
| 2017/0080153 A1 | 3/2017 | Maxfield |
| 2017/0080163 A1 | 3/2017 | Bendek et al. |
| 2017/0106146 A1 | 4/2017 | Folk et al. |
| 2017/0119972 A1 | 5/2017 | Holmqvist |
| 2017/0136189 A1 | 5/2017 | Tschirren et al. |
| 2017/0143902 A1 | 5/2017 | Hansen et al. |
| 2017/0143912 A1 | 5/2017 | Hu |
| 2017/0151393 A1 | 6/2017 | Edwards et al. |
| 2017/0165426 A1 | 6/2017 | Fabien |
| 2017/0173264 A1 | 6/2017 | Bendek et al. |
| 2017/0173271 A1 | 6/2017 | Young et al. |
| 2017/0182242 A1 | 6/2017 | Galitz et al. |
| 2017/0182253 A1 | 6/2017 | Folk et al. |
| 2017/0189619 A1 | 7/2017 | Constantineau et al. |
| 2017/0203041 A1 | 7/2017 | Julian et al. |
| 2017/0216525 A1 | 8/2017 | Chang et al. |
| 2017/0224926 A1 | 8/2017 | Dennis, Jr. et al. |
| 2017/0224927 A1 | 8/2017 | Windum et al. |
| 2017/0224928 A1 | 8/2017 | Högdahl |
| 2017/0232206 A1 | 8/2017 | Blondino et al. |
| 2017/0239418 A1 | 8/2017 | Levine et al. |
| 2017/0239419 A1 | 8/2017 | Mcloughlin et al. |
| 2017/0246393 A1 | 8/2017 | Genosar |
| 2017/0246403 A1 | 8/2017 | Cowe et al. |
| 2017/0259002 A1 | 9/2017 | Laiosa et al. |
| 2017/0274149 A1 | 9/2017 | Aeschlimann |
| 2017/0304538 A1 | 10/2017 | Renstad et al. |
| 2017/0304548 A1 | 10/2017 | Chen et al. |
| 2017/0319791 A1 | 11/2017 | Giambattista et al. |
| 2017/0326298 A1 | 11/2017 | Hourmand et al. |
| 2017/0348491 A1 | 12/2017 | Kiilerich |
| 2017/0361015 A1 | 12/2017 | Mccullough |
| 2017/0361025 A1 | 12/2017 | Cowe |
| 2017/0368260 A1 | 12/2017 | Mccullough et al. |
| 2018/0000691 A1 | 1/2018 | Terhune et al. |
| 2018/0008775 A1 | 1/2018 | Stefanov |
| 2018/0008779 A1 | 1/2018 | Hautaviita et al. |
| 2018/0015223 A1 | 1/2018 | Aeschlimann |
| 2018/0015224 A1 | 1/2018 | Veilleux et al. |
| 2018/0028753 A1 | 2/2018 | Wilmot et al. |
| 2018/0036481 A1 | 2/2018 | Wilmot et al. |
| 2018/0043103 A1 | 2/2018 | Nandigala et al. |
| 2018/0056000 A1 | 3/2018 | Forghani et al. |
| 2018/0056001 A1 | 3/2018 | Forghani et al. |
| 2018/0078703 A1 | 3/2018 | Maxfield |
| 2018/0093045 A1 | 4/2018 | Mehawej et al. |
| 2018/0099093 A1 | 4/2018 | Ebert et al. |
| 2018/0104416 A1 | 4/2018 | Anderson et al. |
| 2018/0110926 A1 | 4/2018 | Schrul et al. |
| 2018/0110927 A1 | 4/2018 | Frias Goyenechea et al. |
| 2018/0117251 A1 | 5/2018 | Rioux et al. |
| 2018/0126082 A1 | 5/2018 | Edwards et al. |
| 2018/0140461 A1 | 5/2018 | Nandigala et al. |
| 2018/0140774 A1 | 5/2018 | Constantineau et al. |
| 2018/0140781 A1 | 5/2018 | Kemp et al. |
| 2018/0140782 A1 | 5/2018 | Kemp et al. |
| 2018/0147352 A1 | 5/2018 | Farmer et al. |
| 2018/0161504 A1 | 6/2018 | Kemp et al. |
| 2018/0169338 A1 | 6/2018 | Mosebach et al. |
| 2018/0169346 A1 | 6/2018 | Hostettler et al. |
| 2018/0177947 A1 | 6/2018 | Brereton et al. |

OTHER PUBLICATIONS

Written Opinion of the International Searching Authority mailed May 23, 2019 in corresponding International Application No. PCT/US2019/014353, 5 pages.

International Preliminary Report on Patentability mailed Jul. 30, 2020 in corresponding International Application No. PCT/US2019/014353, 6 pages.

Examination Report No. 1 dated Nov. 7, 2023 issued in AU Application No. 2019208338, 3 pages.

Foreign Search Report on EP 19740874.3 DTD Sep. 14, 2021.

Communication pursuant to Article 94(3) EPC dated Feb. 28, 2024 issued in EP Application No. 19740874.3, 5 pages.

Office Action dated Jul. 3, 2025 issued in CA Application No. 3,088,749, 4 pages.

Examination Report No. 1 dated Dec. 1, 2025 issued in AU Application No. 2024227540, 3 pages.

* cited by examiner

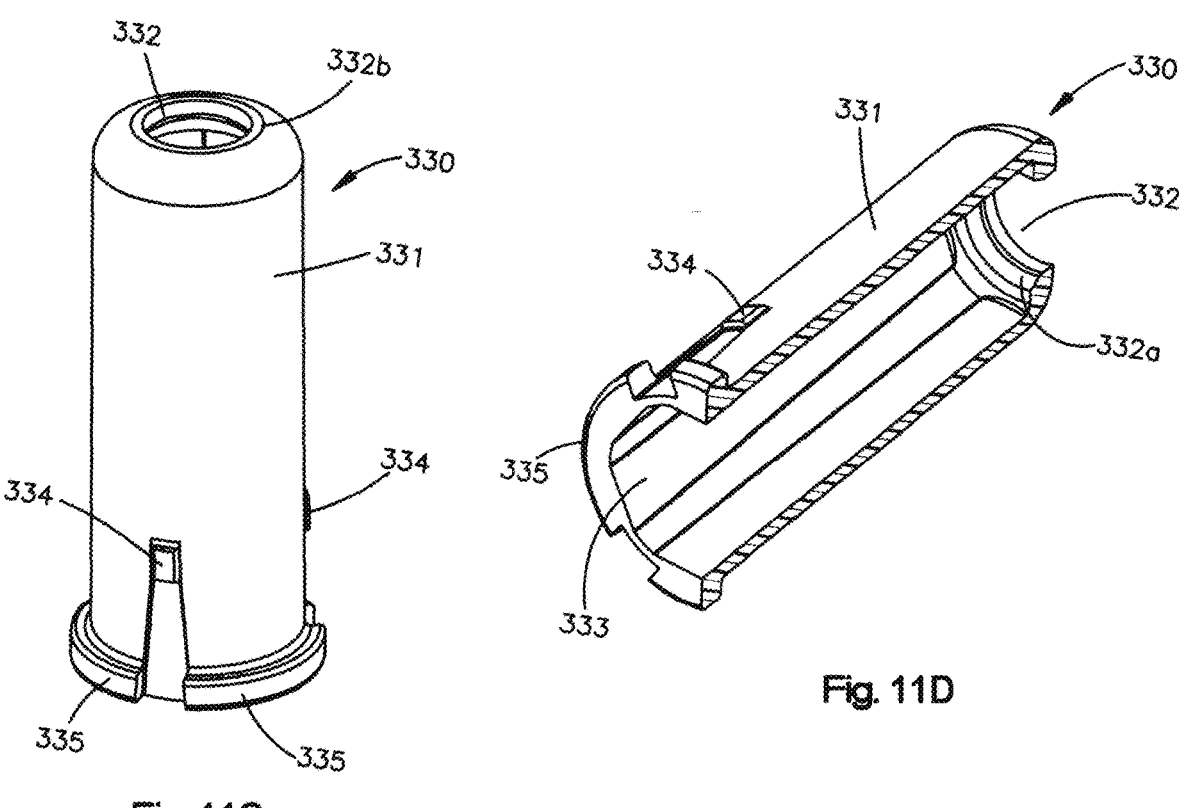
Fig. 11C
Fig. 11D
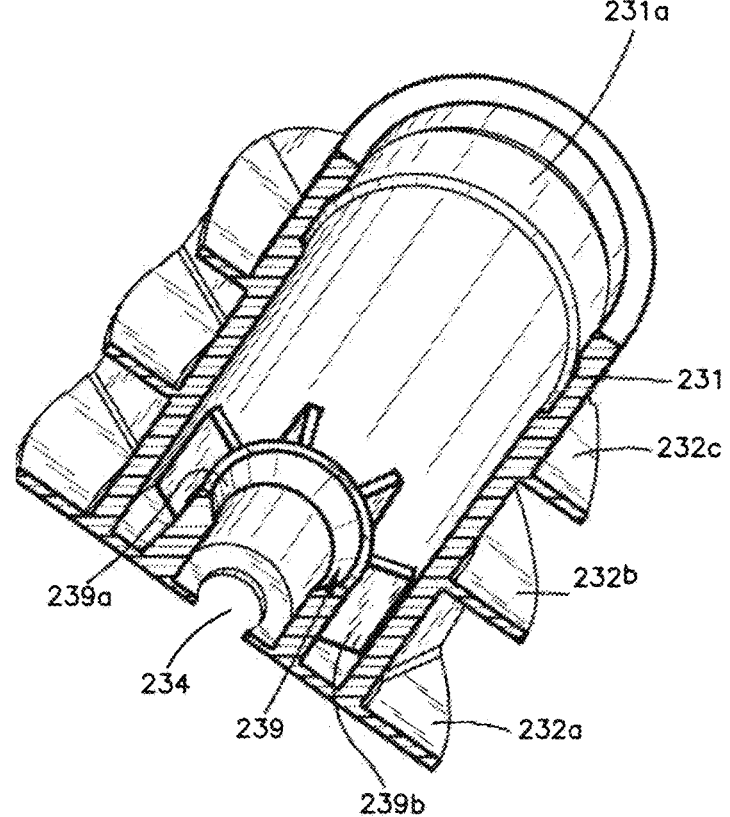
Fig. 11B

TOOL FOR SERVICING AN AUTO-INJECTOR

CROSS-REFERENCE TO RELATED APPLICATIONS

This application is a U.S. National Stage of International Application No. PCT/US2019/014353 filed on Jan. 18, 2019, which claims the benefit of U.S. Provisional Application Ser. No. 62/619,236 filed Jan. 19, 2018, the entire disclosures of all of which are incorporated herein by reference.

FIELD

The present disclosure relates to servicing medical devices. More particularly, the present disclosure relates to a method and apparatus for opening auto-injectors for refilling with medicament upon activation. Disclosed embodiments provide for reassembling the auto-injector as a functional medical device for subsequent service.

BACKGROUND

An automatic injector or auto-injector is a device designed to allow a user to self-administer a pre-measured dose of a medicament composition subcutaneously or intramuscularly, often in an emergency situation. Automatic injectors are used for example, to treat anaphylactic (severe allergic) reactions and to administer antidotes for certain poisons, such as chemical nerve agents and various drug compositions such as diazepan.

Thus, an auto-injector automatically dispenses a predetermined dose of medicament upon activation. The auto-injector may include a needle cover operative to engage an injection site and activate the injector. The needle cover may be configured to move from a locked retracted position prior to a medicament dispensing operation to a locked extended position after the medicament dispensing operation. The non-removable needle cover may prevent contact with the needle both before and after the medicament dispensing operation.

Auto-injectors are constructed to be tamper proof and resistant to damage while also being intended for disposal after use or expiry. Such disposal of auto-injectors after use or expiry produces large amounts of waste material and does not contribute to cost efficacy. Thus, there is a need for providing a method and apparatus for opening, disassembling and reassembling auto-injectors in a manner that enables the medical devices to be easily serviced and reassembled in a manner that is conducive to being refilled and reliably used.

SUMMARY

In at least one embodiment, an apparatus for servicing an auto-injector is provided. The apparatus includes a base; a receiver coupled to the base and configured to accommodate the auto-injector therein; a clamp coupled to the base and configured to move from a first position in which the clamp is in a non-clamped state to a second position in which the clamp is in a clamped state, wherein, in the clamped state, the clamp is configured to compress the auto-injector; and an extractor coupled to the base and including a coupling device structured to couple to an actuation assembly of the auto-injector, the extractor being configured to pull the actuation assembly out of the auto-injector with the coupling device.

In at least one embodiment, a method of servicing an auto-injector is provided. The method includes inspecting the auto-injector to determine whether the auto-injector is serviceable; removing, via an apparatus, an actuation assembly from a body of the auto-injector; disposing of existing medicament from the auto-injector; refilling the auto-injector with medicament; and re-inserting the actuation assembly into the auto-injector and closing the auto-injector to render the auto-injector serviceable for further deployment.

In at least one embodiment, a method of using a tool for servicing an auto-injector, is provided. The method includes placing the auto-injector in a receiver of the tool; moving a clamp coupled to a base from a first position to a second position, the first position being a position in which the clamp is in a non-clamped state and the second position being a position in which the clamp is in a clamped state, wherein, in the clamped state, the clamp is configured to compress the auto-injector; and coupling at least a portion of an extractor to the auto-injector to pull an actuation assembly out of the auto-injector with the coupled extractor.

BRIEF DESCRIPTION OF THE DRAWINGS

The accompanying drawings, which are incorporated herein and constitute part of this specification, illustrate exemplary embodiments of the disclosure, and, together with the general description given above and the detailed description given below, serve to explain the features of the disclosure.

3

FIG. 11B is a partial cross sectional perspective view of the power pack inner body for the exemplary power pack for the auto-injector, according to an embodiment of the present disclosure.

FIG. 11C is a partial cross sectional perspective view of the power pack inner body for the exemplary power pack for the auto-injector, according to an embodiment of the present disclosure.

FIG. 11D is a side perspective view of the power pack inner body for the exemplary power pack for the auto-injector, according to an embodiment of the present disclosure.

Figures 10, 11A, 12, 13:
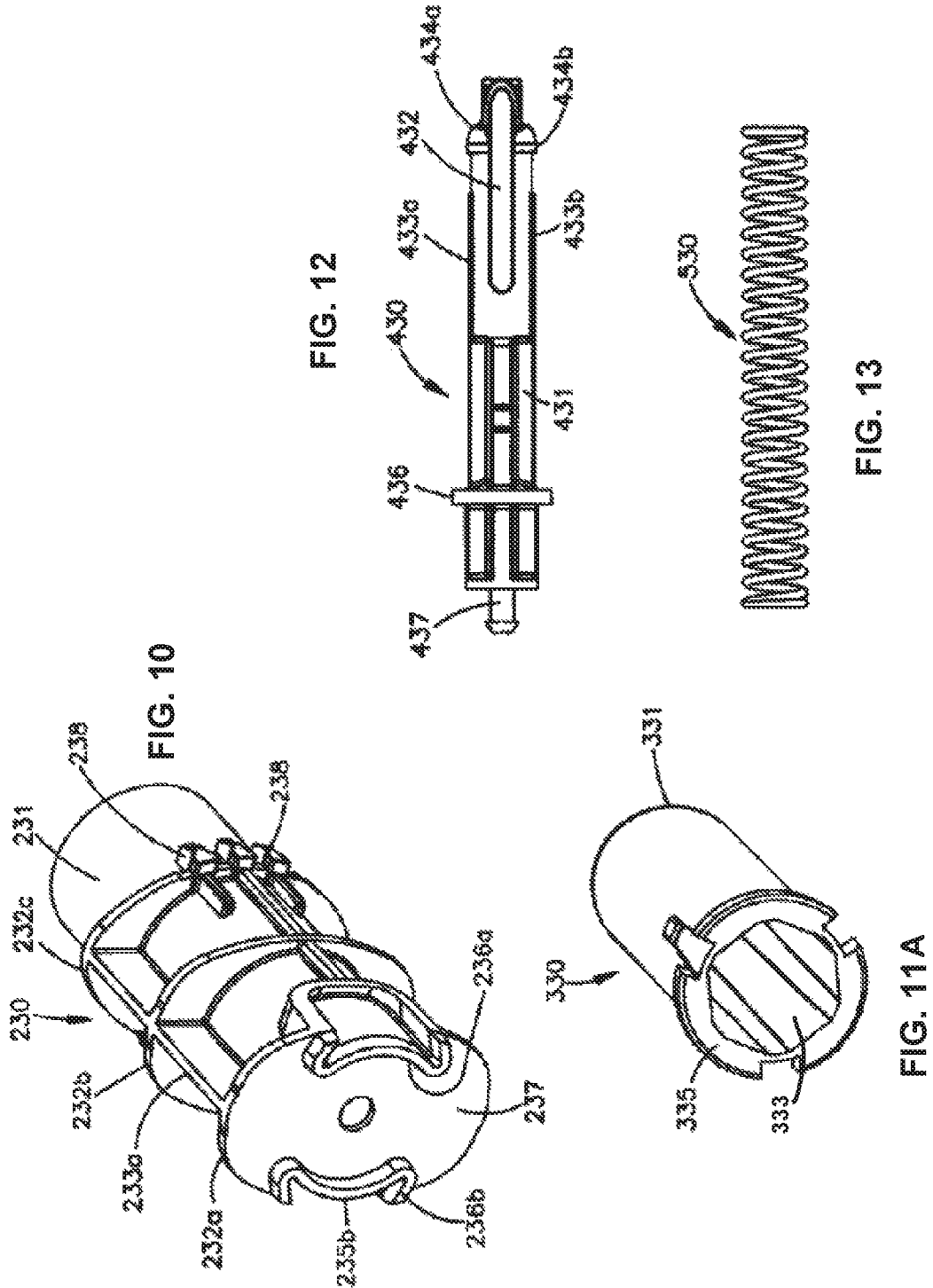
FIG. 10 is a left rear perspective view of the power pack outer body for an exemplary power pack for the auto-injector, according to an embodiment of the present disclosure.
FIG. 11A is a right front perspective view of the power pack inner body for the exemplary power pack for the auto-injector, according to an embodiment of the present disclosure.

FIG. 12 is a side perspective view of the collet for the exemplary power pack for the auto-injector, according to an embodiment of the present disclosure.

FIG. 13 is a side perspective view of the spring assembly for the exemplary power pack for the auto-injector, according to an embodiment of the present disclosure.

Figures 14, 15:
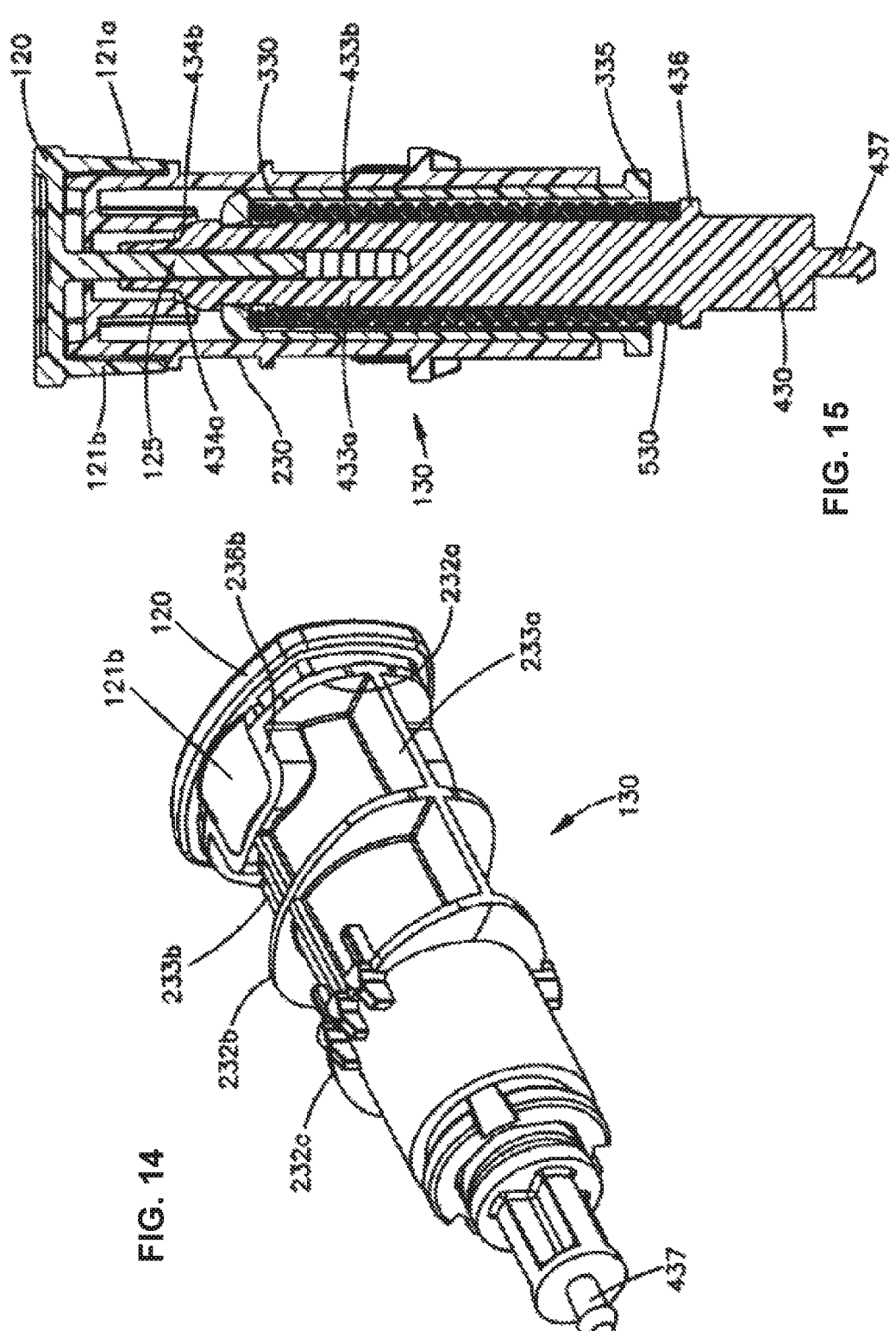

FIG. 14 is a right bottom perspective view of an exemplary power pack of the auto-injector in an assembled state, according to an embodiment of the present disclosure.

FIG. 15 is a side cross sectional view of the exemplary power pack of FIG. 14, according to an embodiment of the present disclosure.

Figures 16, 17, 18:
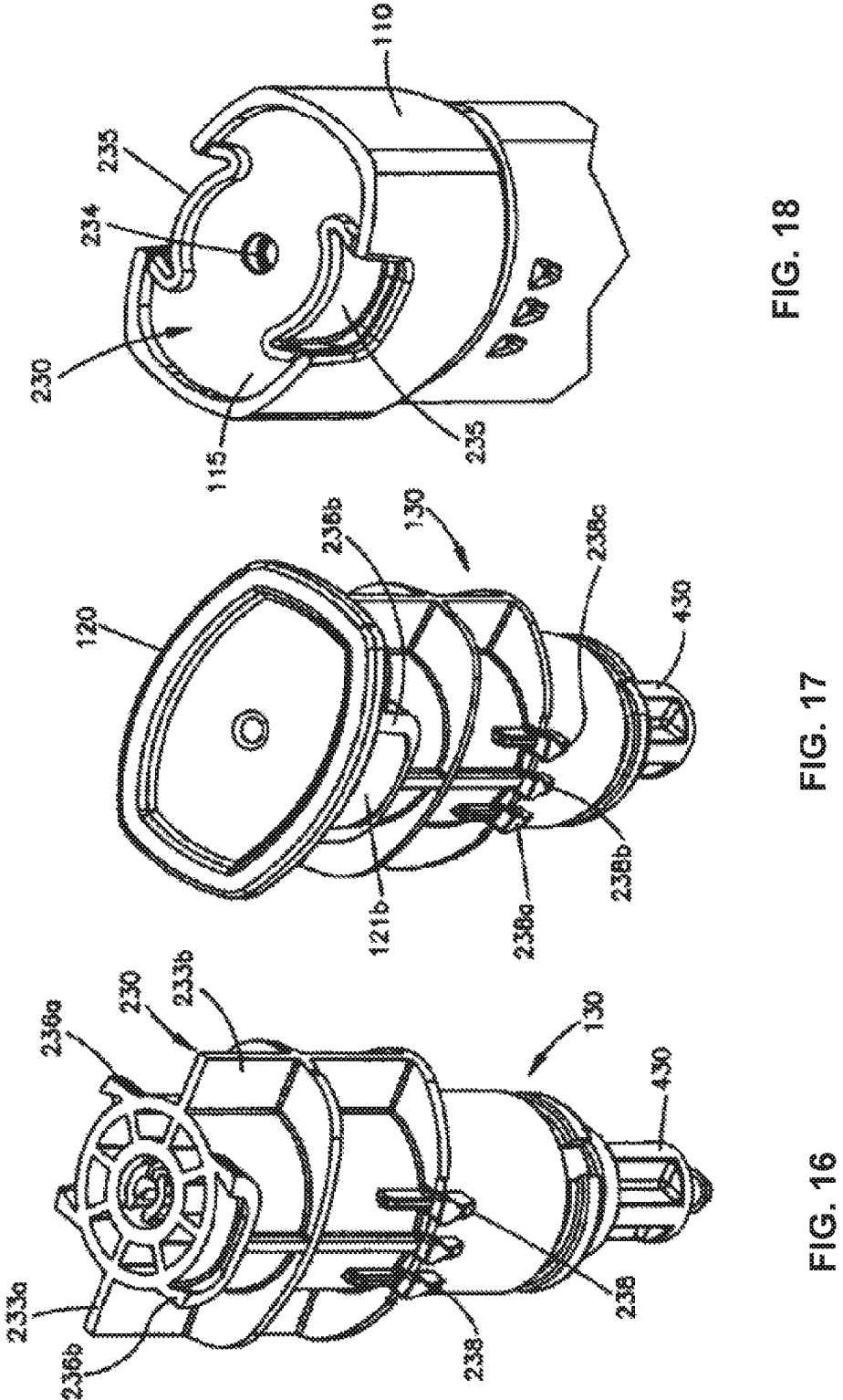

FIG. 16 is a top left perspective view of the exemplary power pack of FIG. 14 having the top portion of the release pin and a peripheral rib of the power pack outer body removed, according to an embodiment of the present disclosure.

FIG. 17 is a top left perspective view of the exemplary power pack of FIG. 14, according to an embodiment of the present disclosure.

FIG. 18 is a top left perspective view of the exemplary power pack positioned within the outer body having the safe pin removed, according to an embodiment of the present disclosure.

Figure 19:
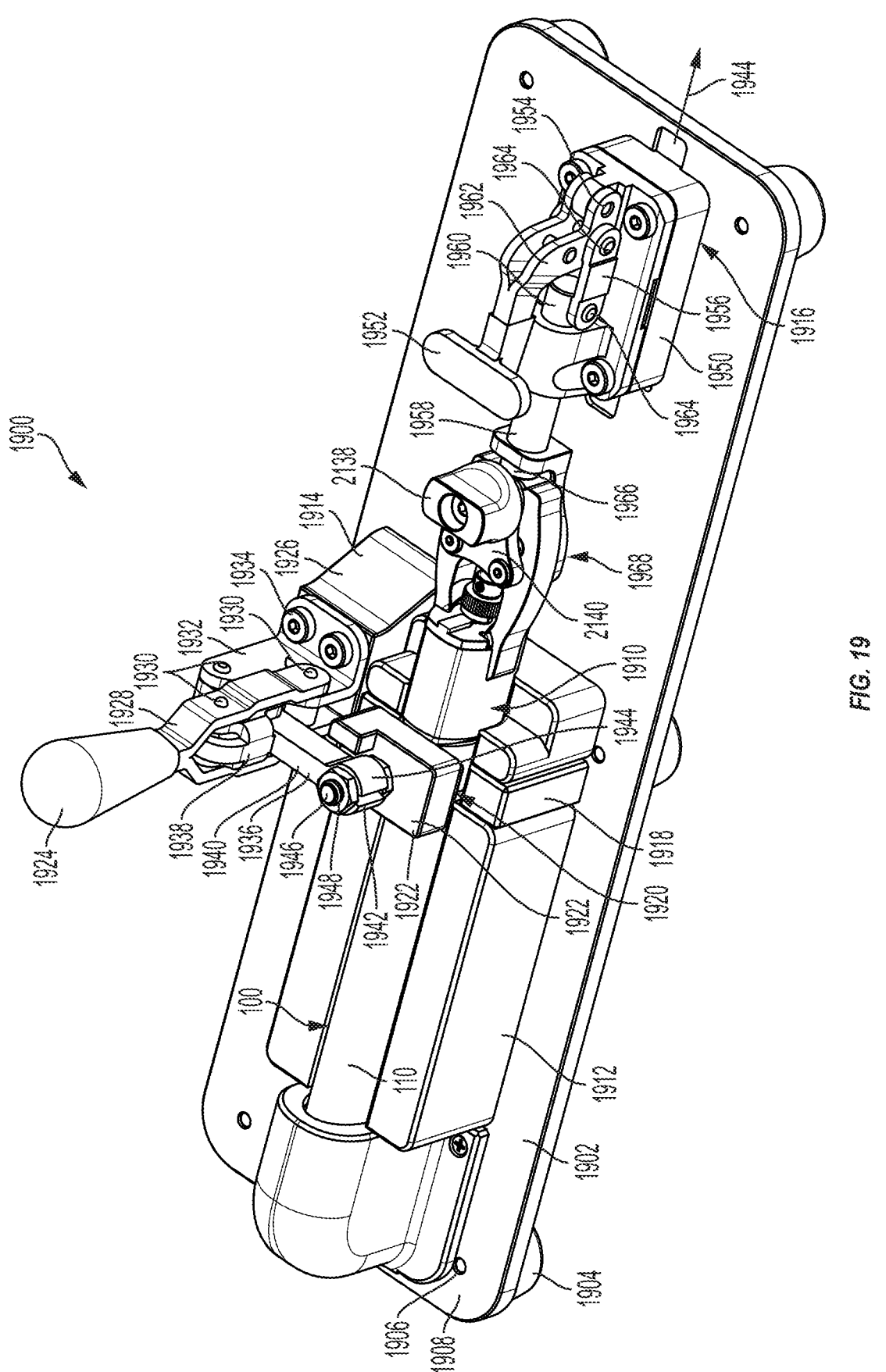

FIG. 19 illustrates a perspective view of an apparatus for servicing an auto-injector, according to an embodiment of the present disclosure.

Figure 20:
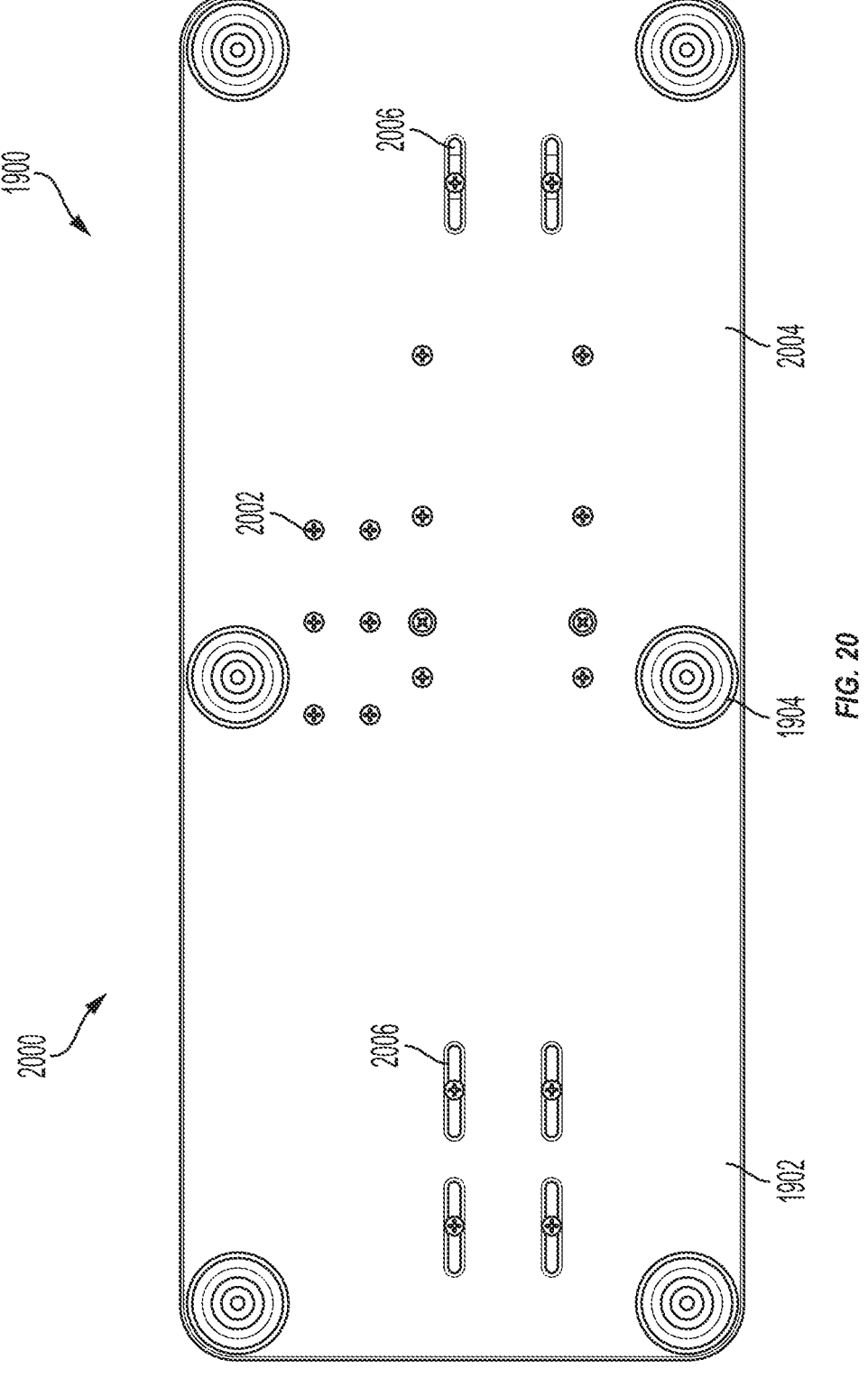

FIG. 20 illustrates a bottom view of the apparatus of FIG. 19 for servicing an auto-injector, according to an embodiment of the present disclosure.

Figure 21:
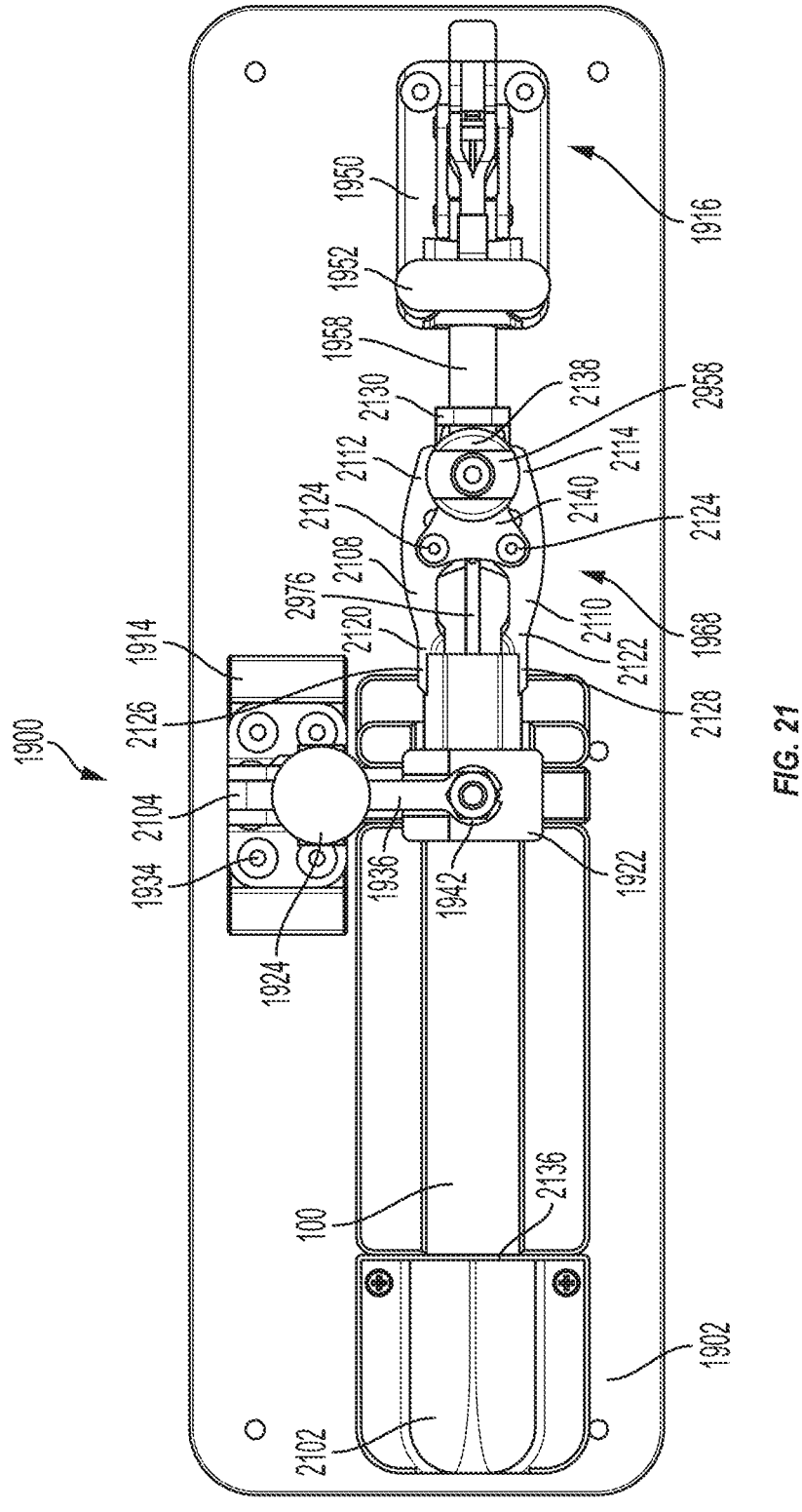

FIG. 21 illustrates a top view of the apparatus of FIG. 19 for servicing an auto-injector, according to an embodiment of the present disclosure.

Figure 22:
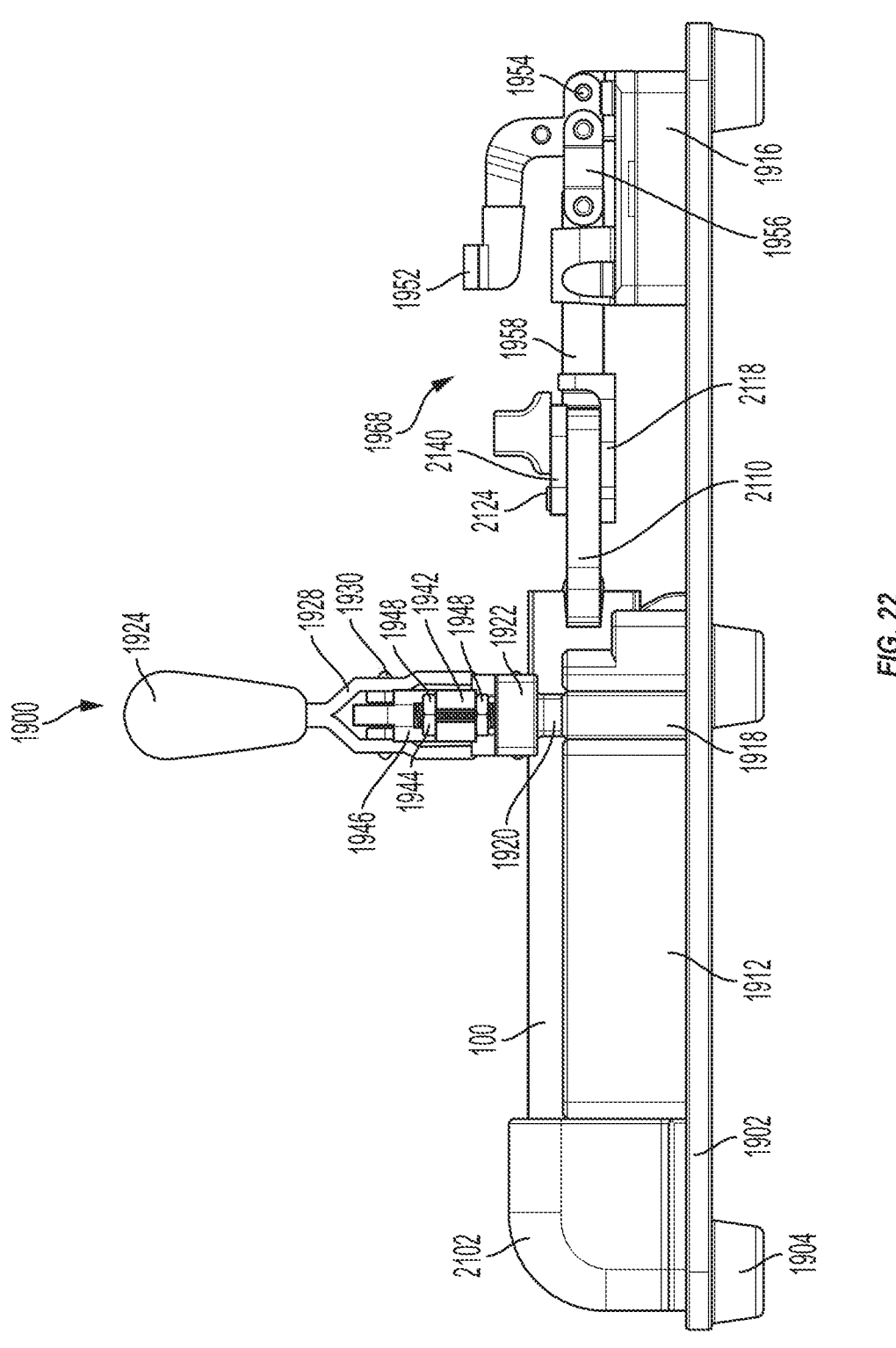

FIG. 22 illustrates a front view of the apparatus of FIG. 19 for servicing an auto-injector, according to an embodiment of the present disclosure.

Figure 23:
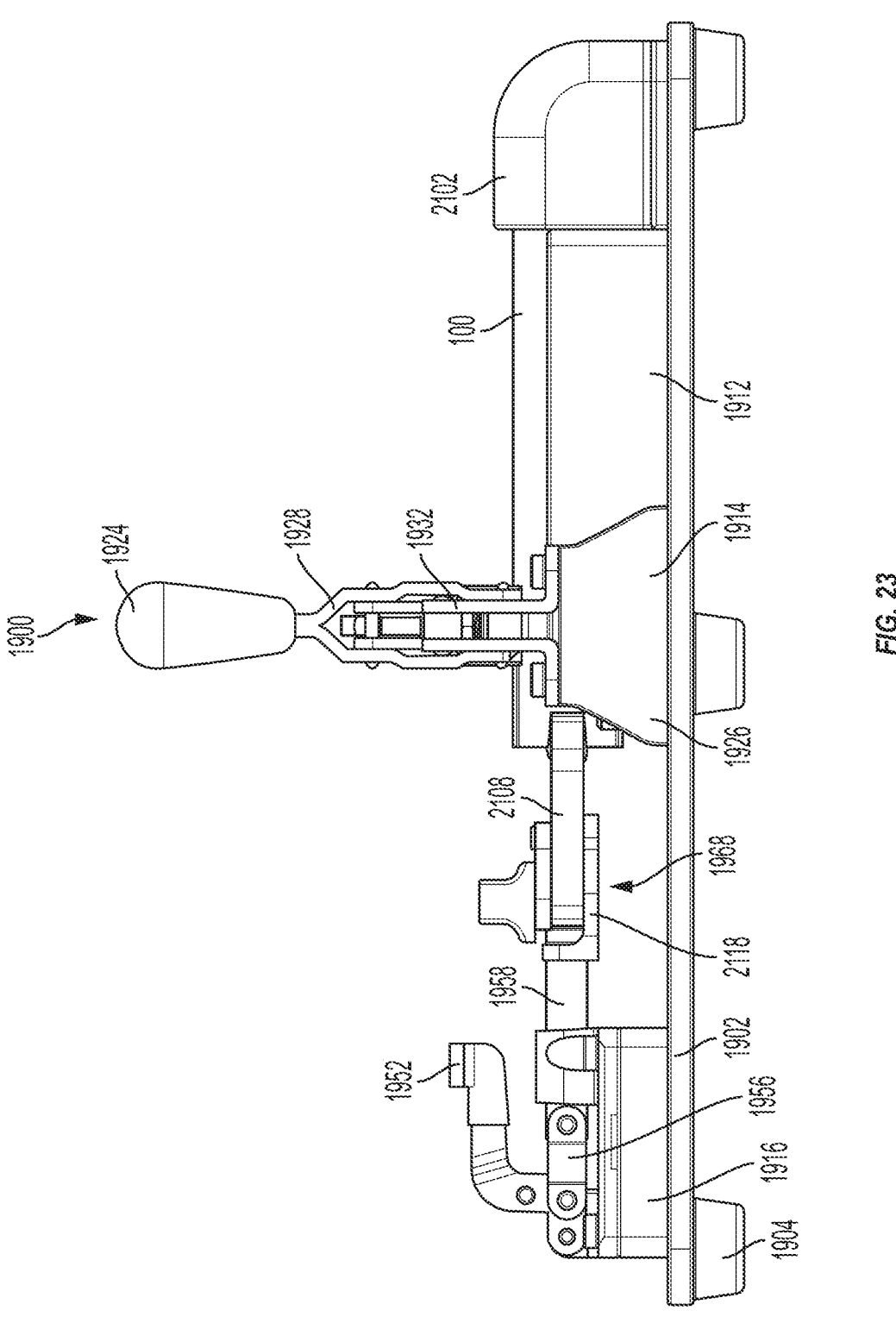

FIG. 23 illustrates a back view of the apparatus of FIG. 19 for servicing an auto-injector, according to an embodiment of the present disclosure.

Figure 24:
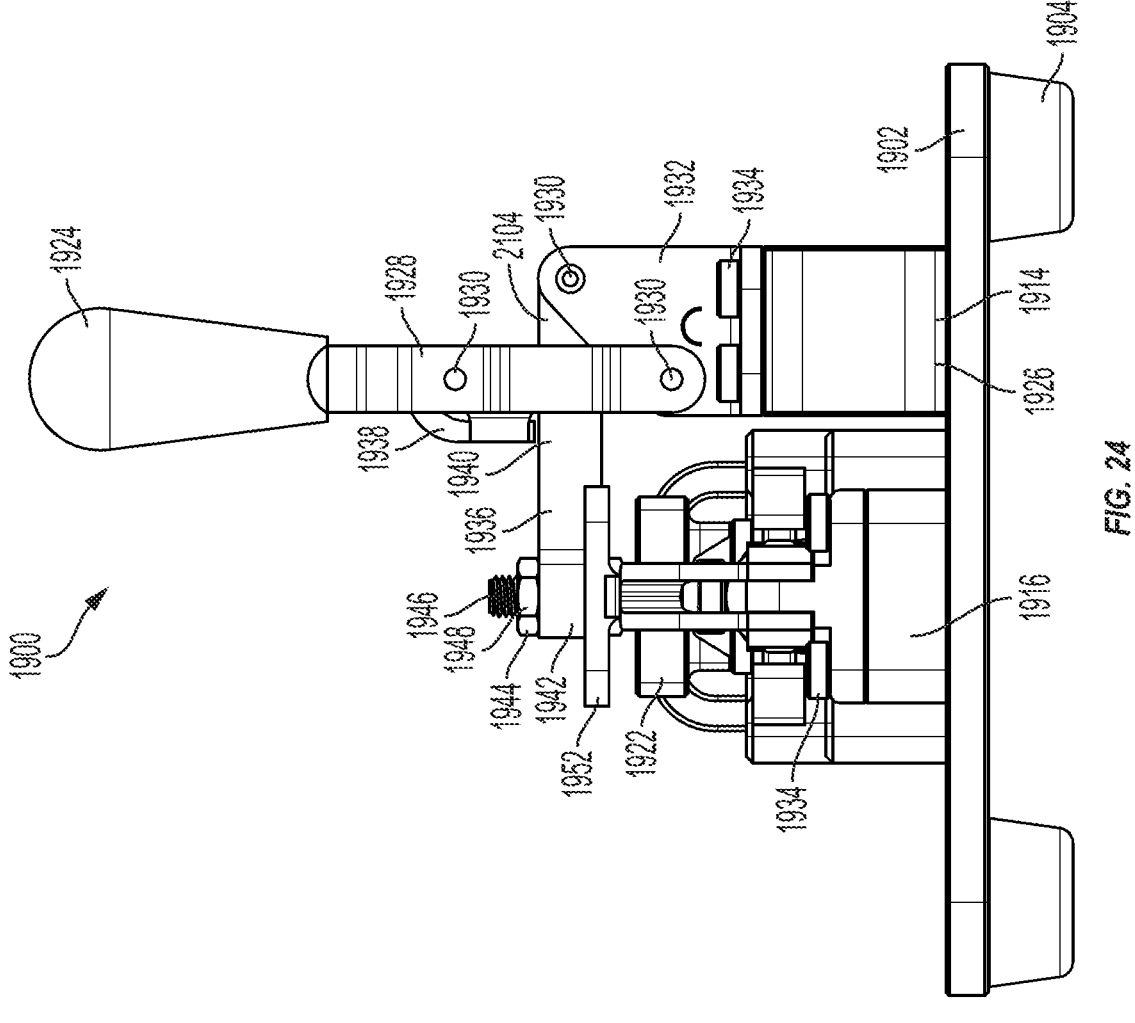

FIG. 24 illustrates a right end view of the apparatus of FIG. 19 for servicing an auto-injector, according to an embodiment of the present disclosure.

Figure 25:
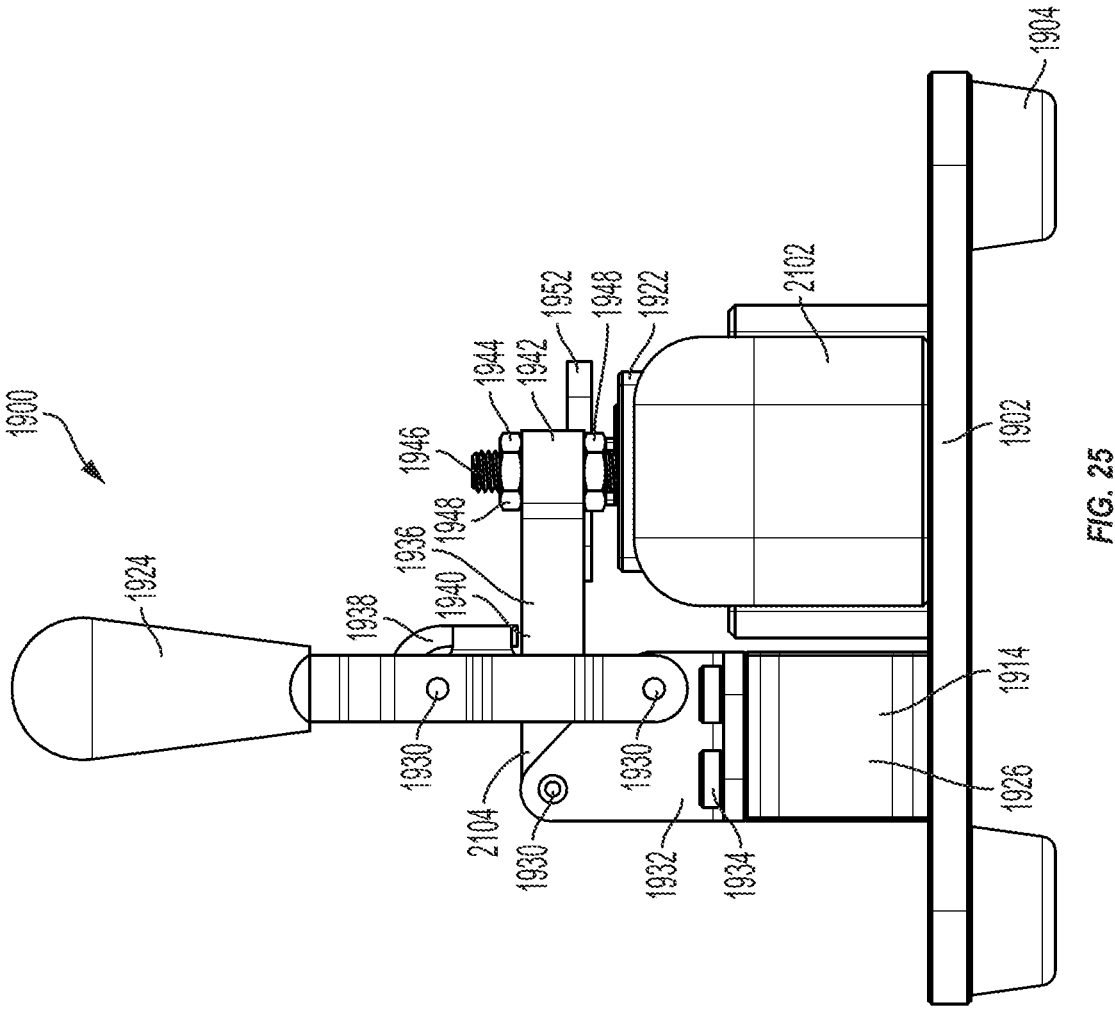

FIG. 25 illustrates a left end view of the apparatus of FIG. 19 for servicing an auto-injector, according to an embodiment of the present disclosure.

Figure 26:
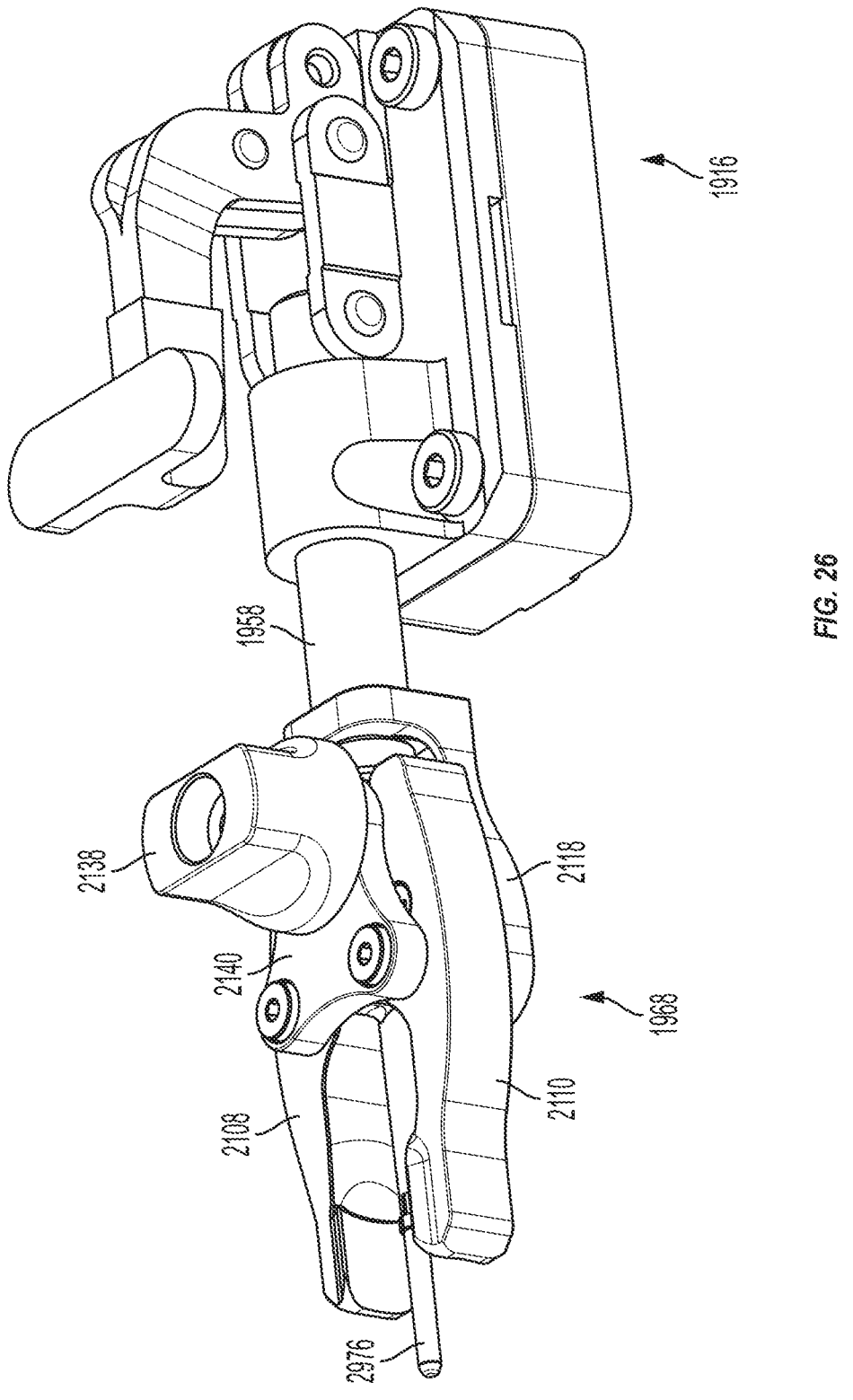

FIG. 26 is an enlarged view of the extractor clamp assembly and extractor handle assembly of the apparatus of FIG. 19 for servicing an auto-injector, according to an embodiment of the present disclosure.

Figure 27:
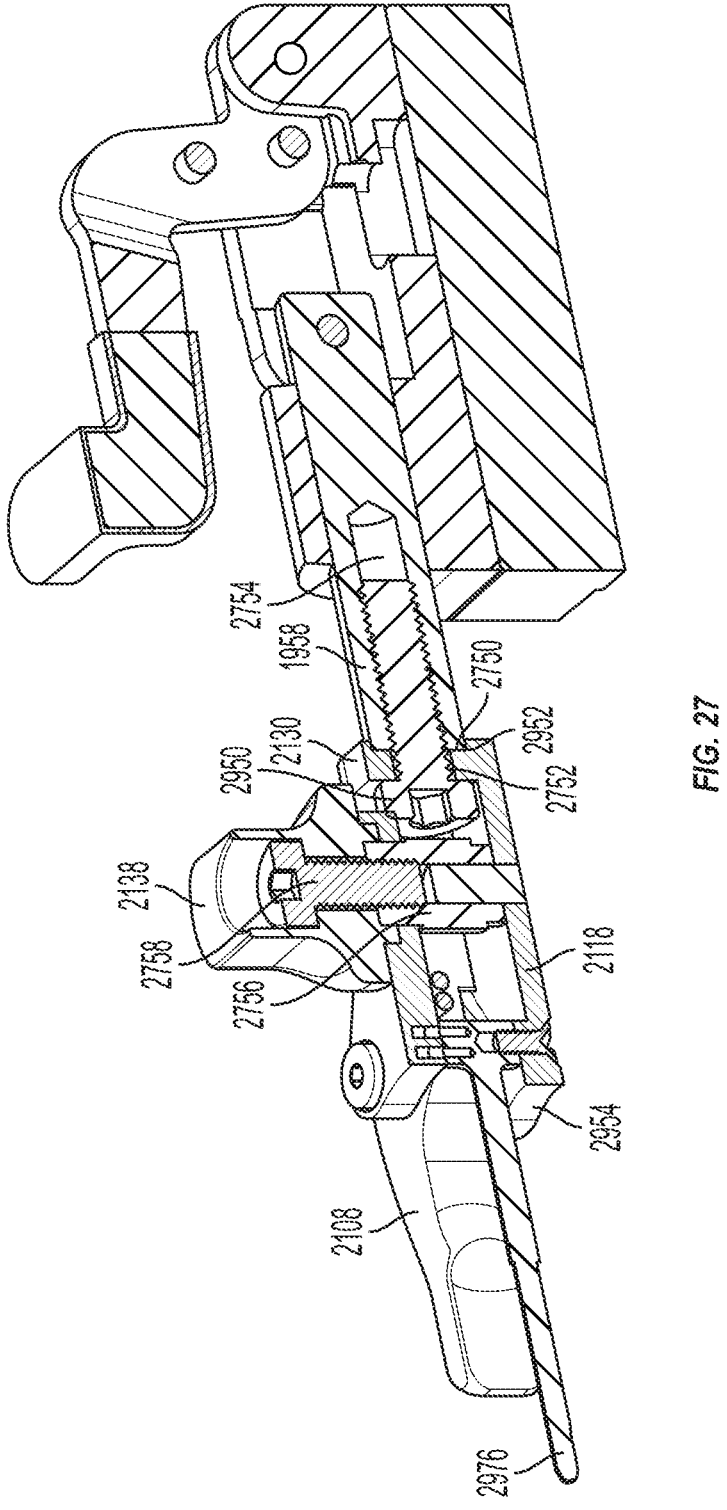

FIG. 27 is a cross-cut view of the extractor clamp assembly and extractor handle assembly of FIG. 26, according to an embodiment of the present disclosure.

Figure 28:
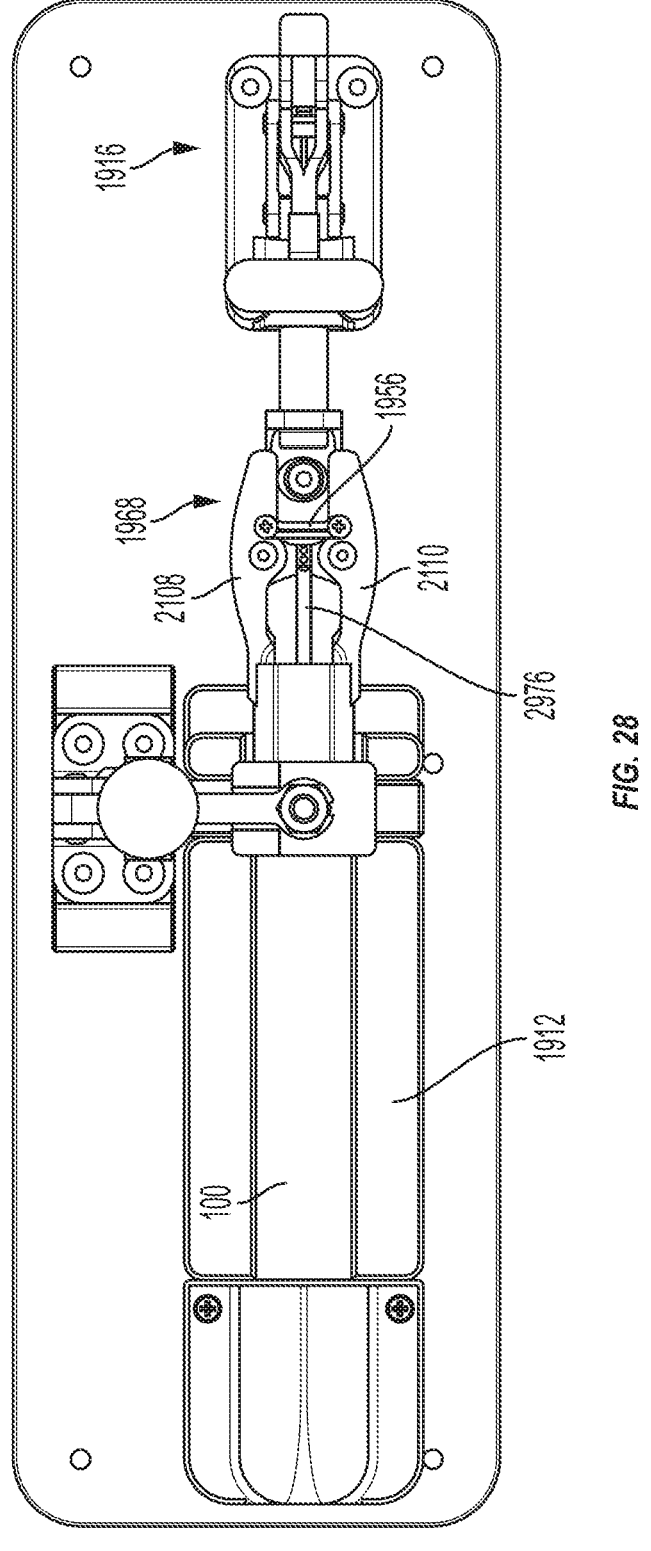

FIG. 28 illustrates a modified top view of the apparatus of FIG. 19 for servicing an auto-injector, according to an embodiment of the present disclosure.

4

Figure 29:
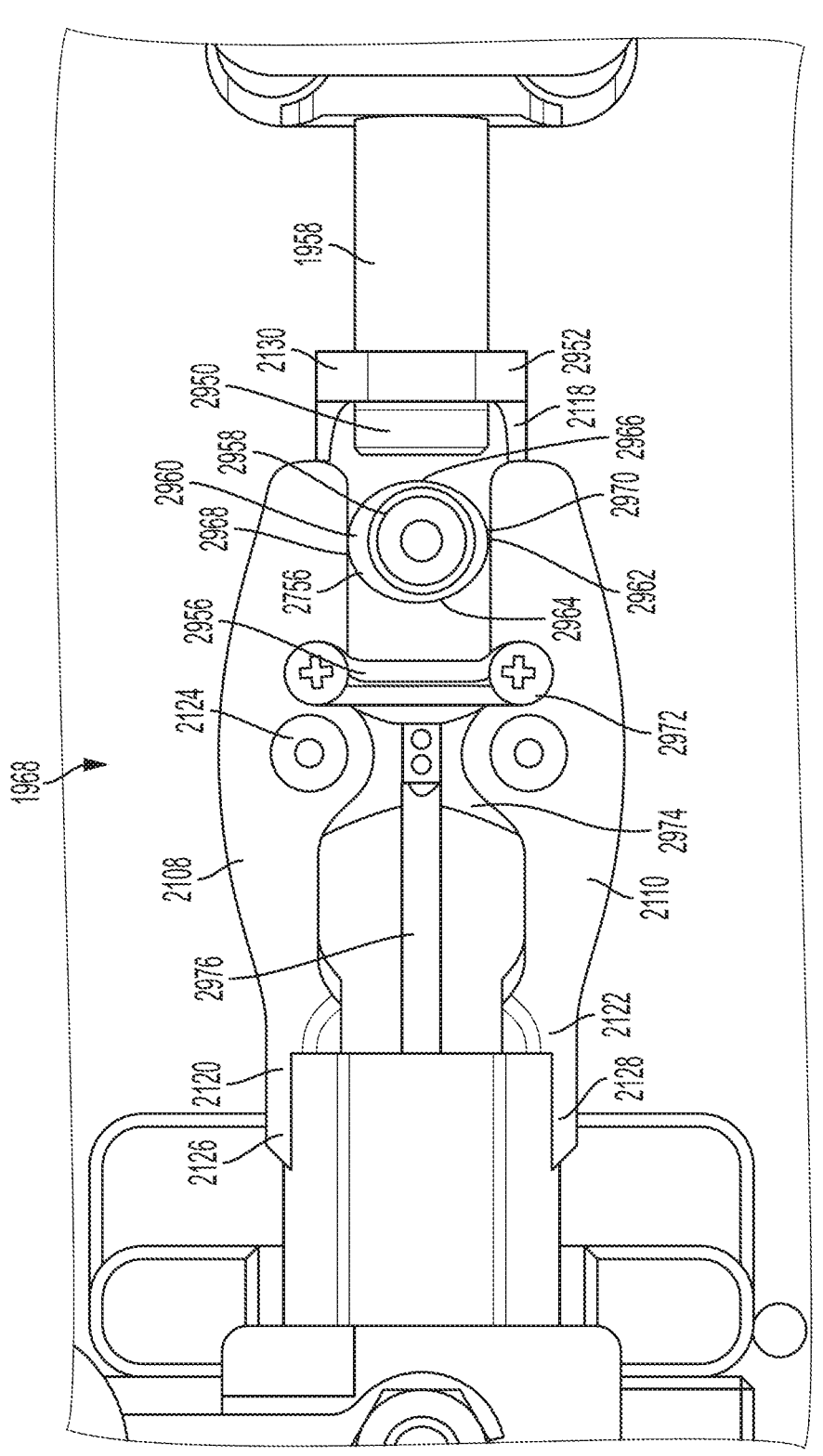

FIG. 29 is an enlarged view of the extractor clamp assembly of FIG. 28, according to an embodiment of the present disclosure.

Figure 30:
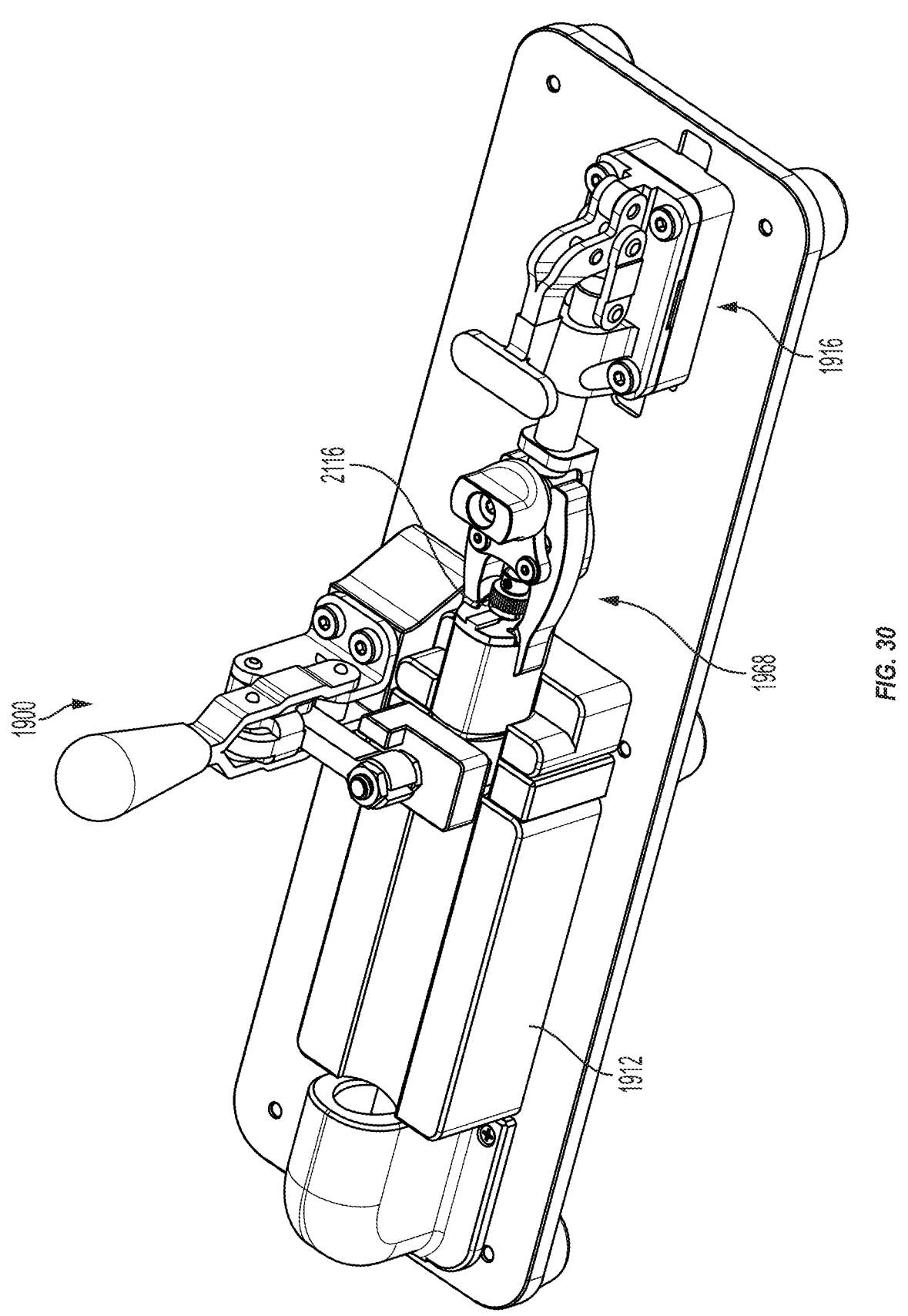

FIG. 30 illustrates a perspective view of another embodiment of an apparatus for servicing an auto-injector, according to an embodiment of the present disclosure.

Figure 31:
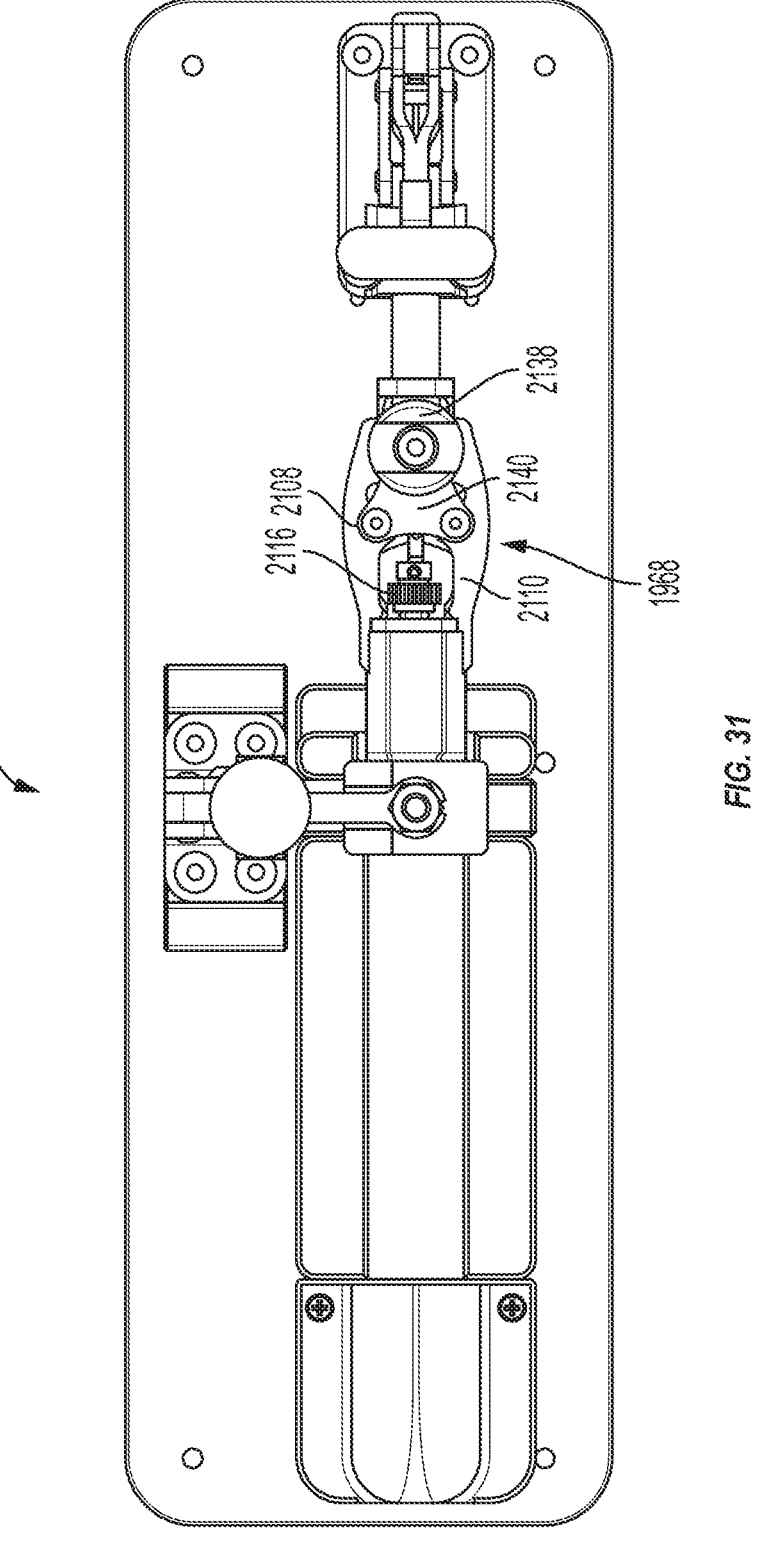

FIG. 31 illustrates a top view of the apparatus of FIG. 30 for servicing an auto-injector, according to an embodiment of the present disclosure.

Figure 32:
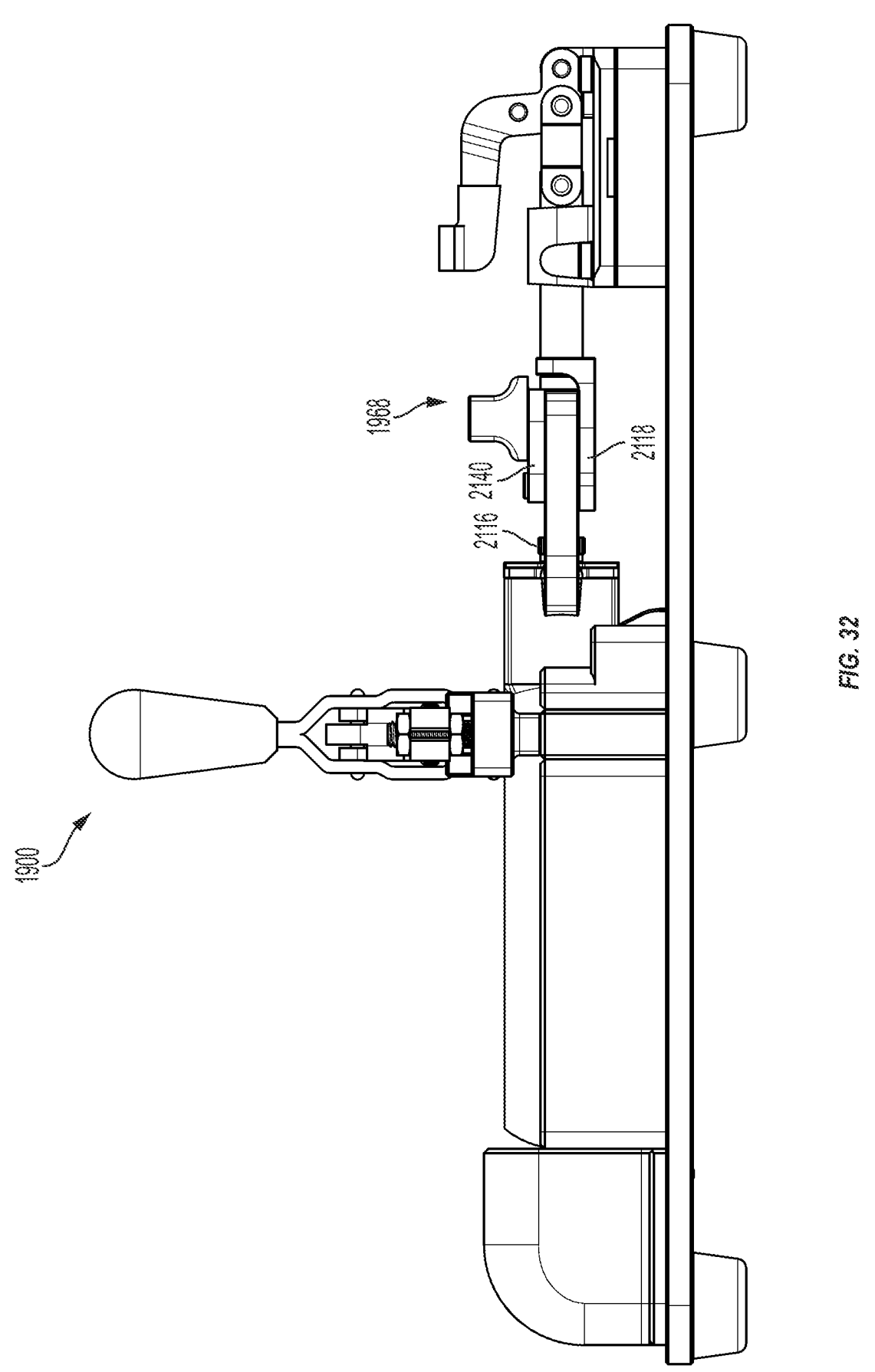

FIG. 32 illustrates a front view of the apparatus of FIG. 30 for servicing an auto-injector, according to an embodiment of the present disclosure.

Figure 33:
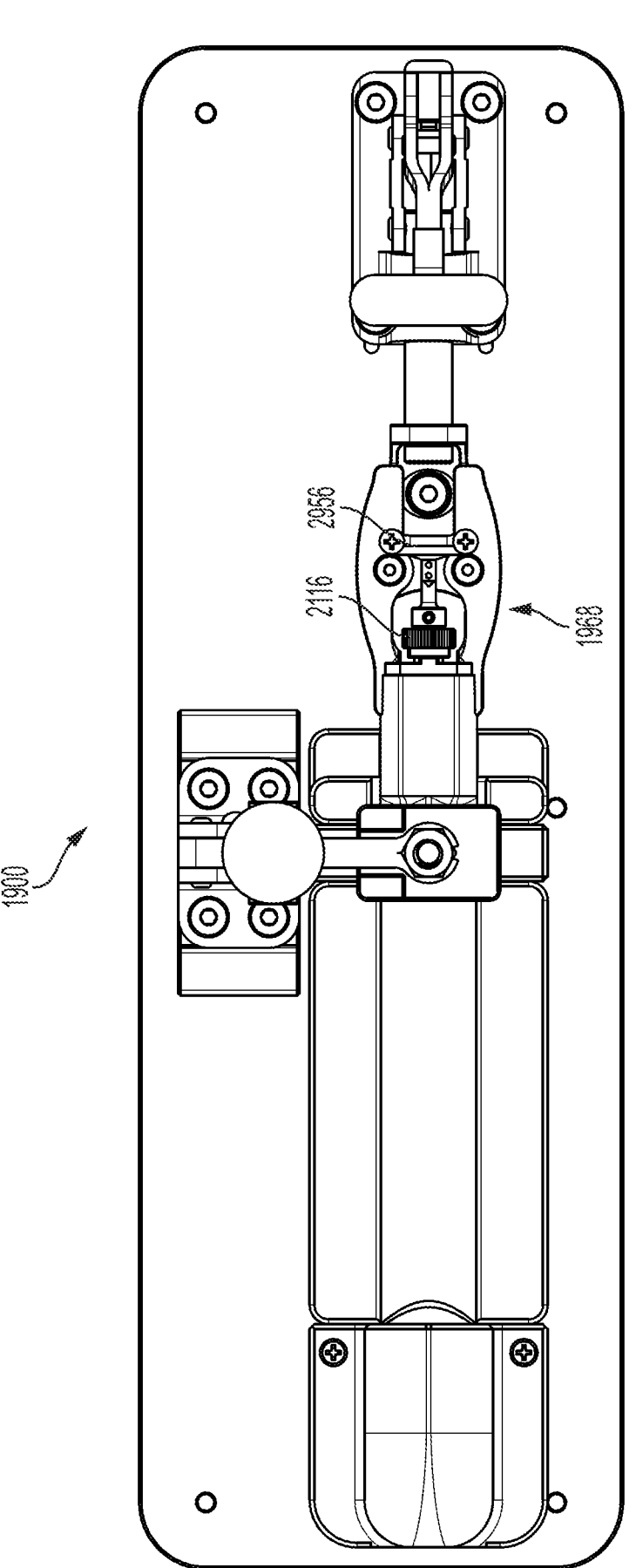

FIG. 33 illustrates a modified top view of the apparatus of FIG. 30 for servicing an auto-injector, according to an embodiment of the present disclosure.

Figure 34:
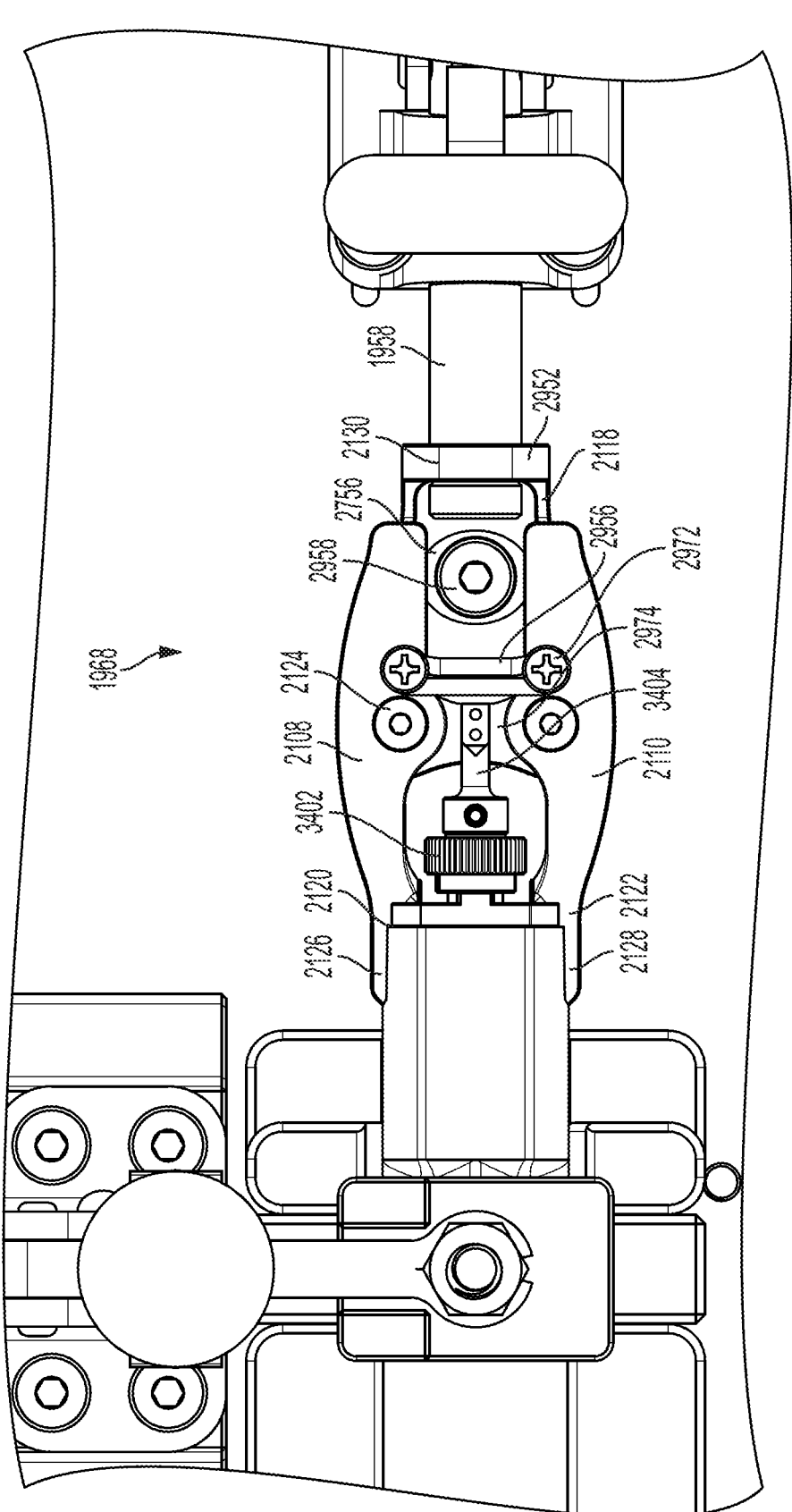

FIG. 34 is an enlarged view of the extractor clamp assembly of FIG. 33, according to an embodiment of the present disclosure.

Figure 35:
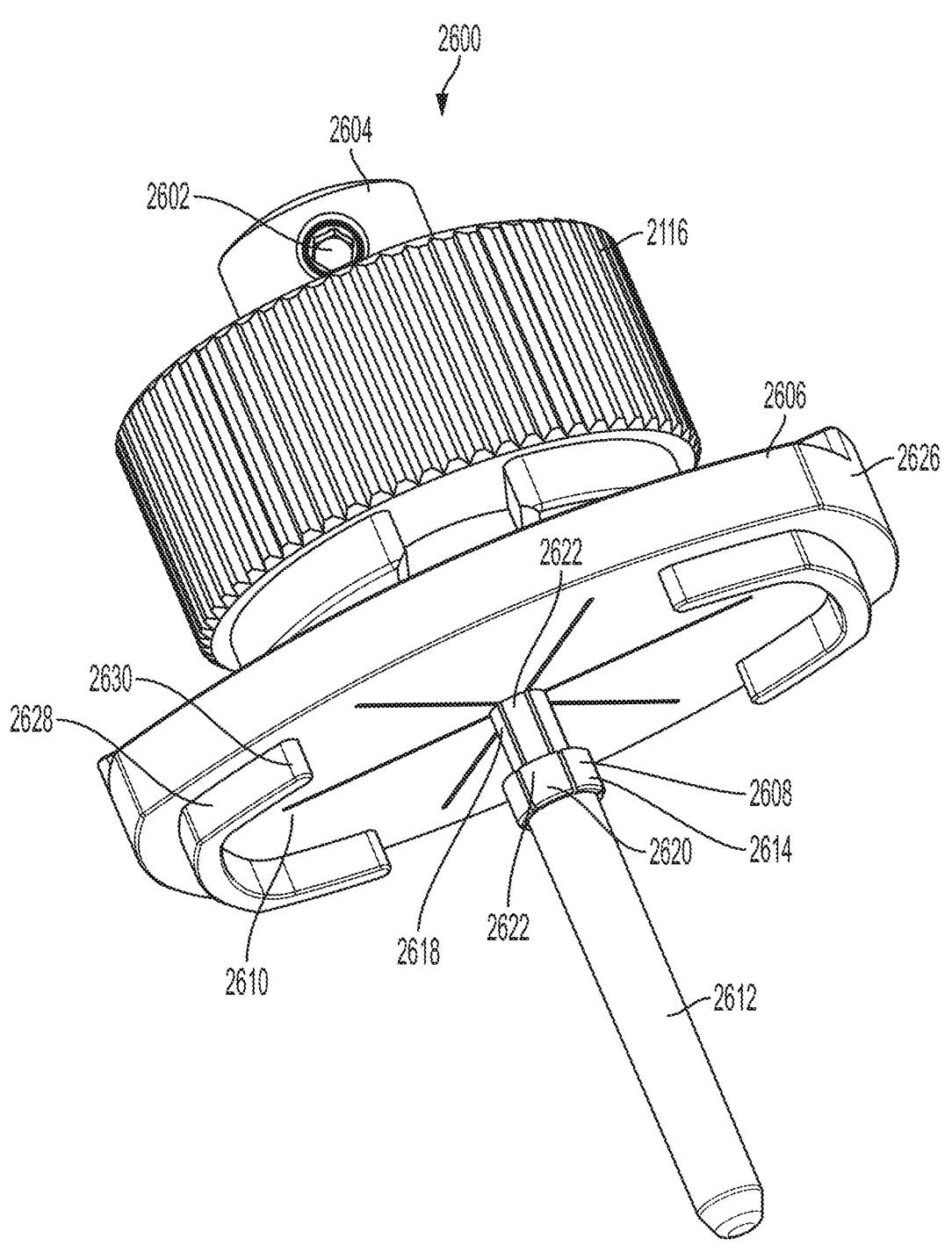

FIG. 35 is a bottom perspective view of a mandrel safety pin assembly employed by the apparatus of FIG. 30 for servicing the auto-injector, according to an embodiment of the present disclosure.

Figure 36:
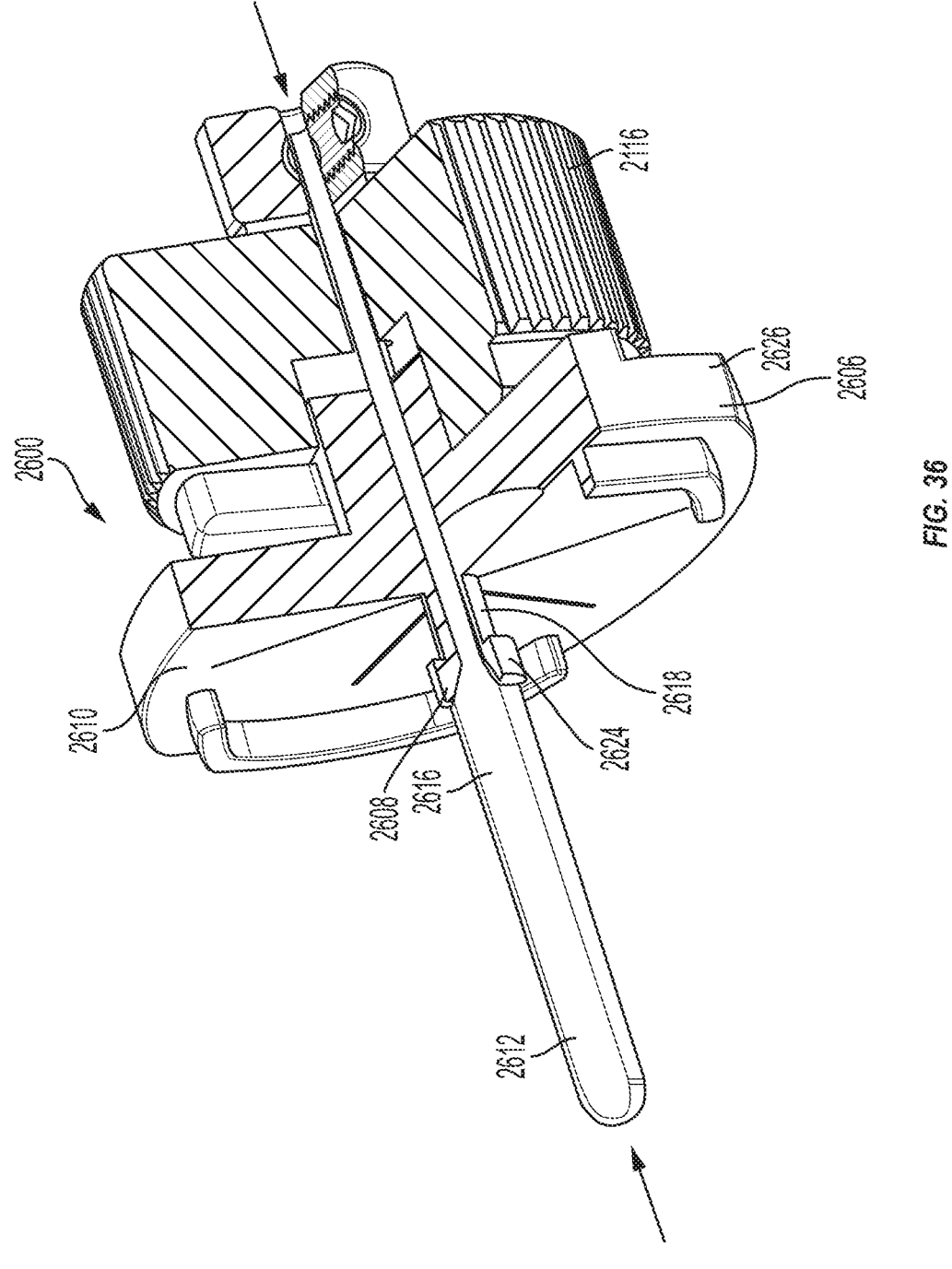

FIG. 36 is a cut-away view of the mandrel safety pin assembly of FIG. 35, according to an embodiment of the present disclosure.

Figure 37:
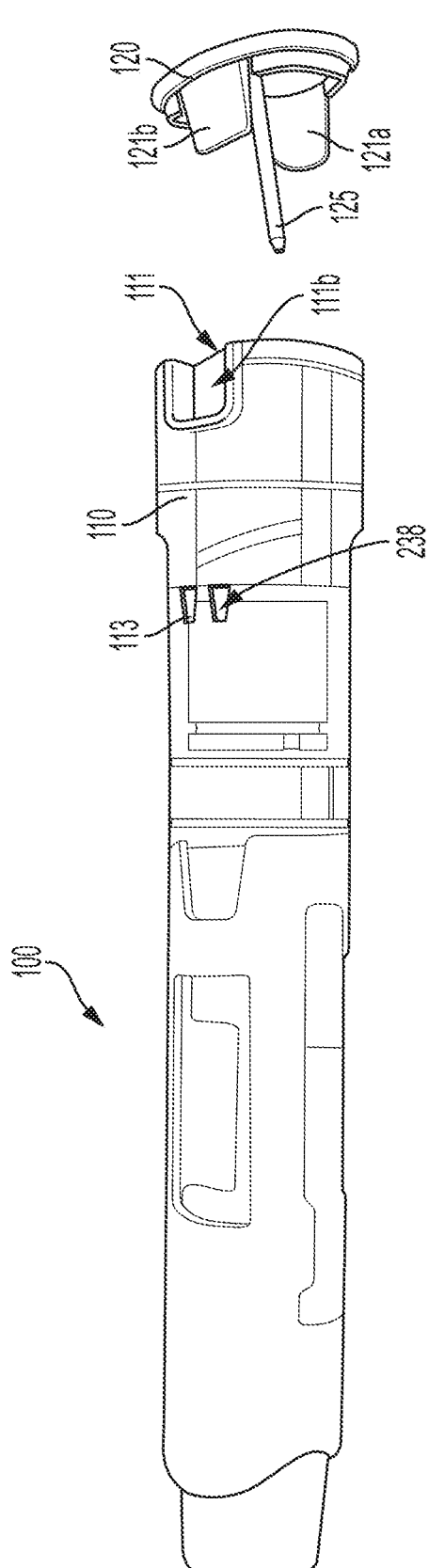

FIG. 37 illustrates a safe release pin removed from an exemplary auto-injector, according to an embodiment of the present disclosure.

Figure 38:
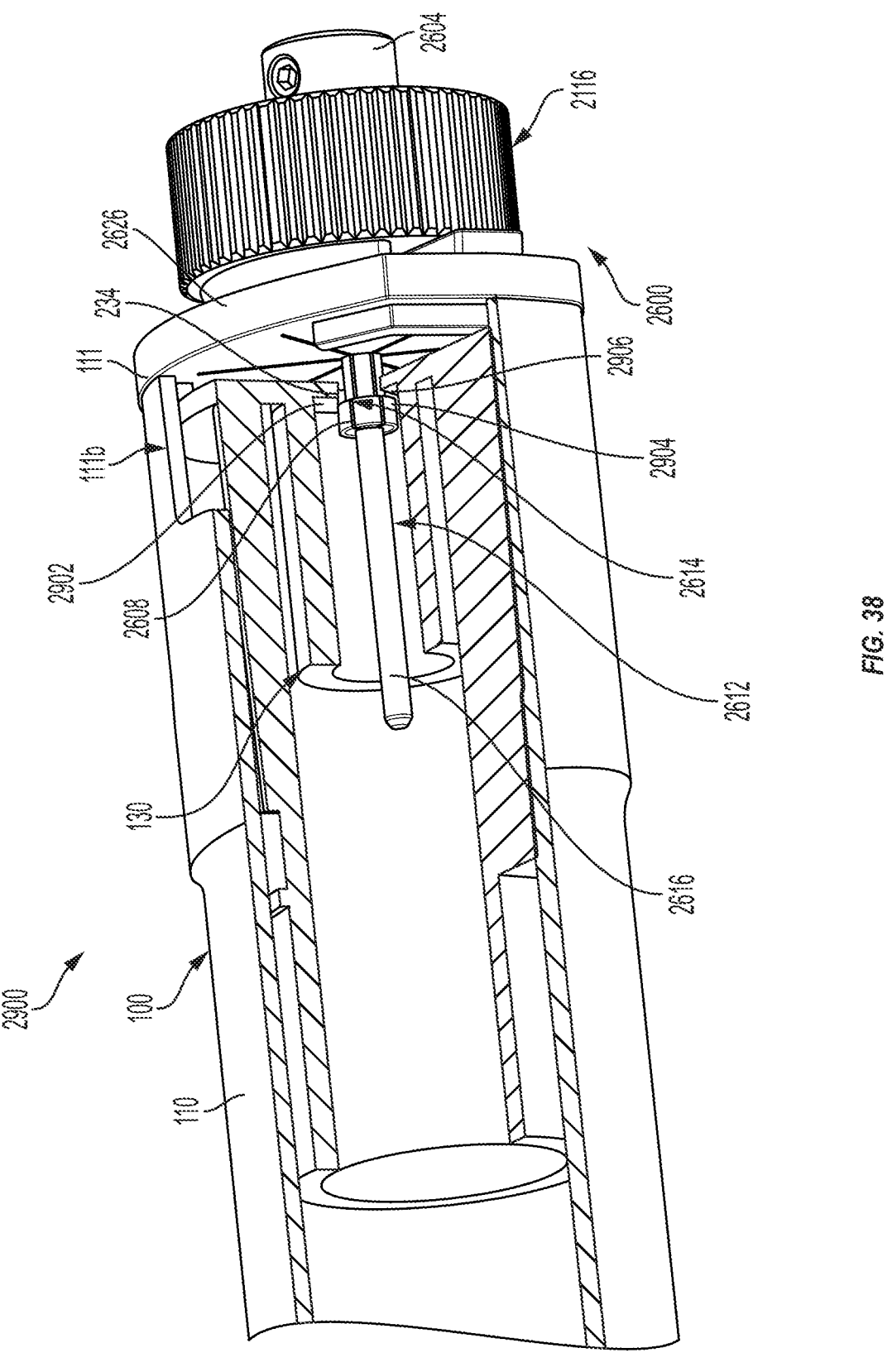

FIG. 38 is a cut-away view of the mandrel safety pin assembly in connection with the power pack of the auto-injector, according to an alternate embodiment of the present disclosure.

Figure 39:
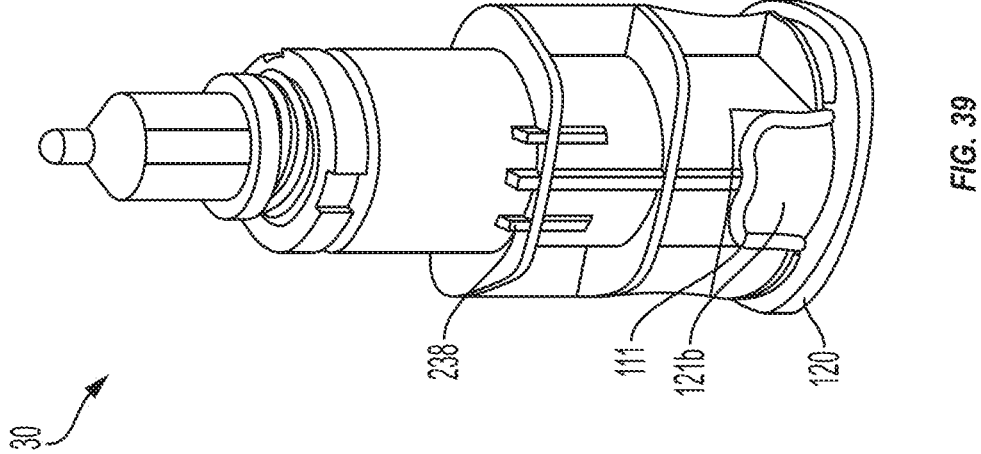

FIG. 39 illustrates an exemplary power pack removed from the auto-injector body by the apparatus of FIGS. 19 and 30, according to an embodiment of the present disclosure.

Figure 40:
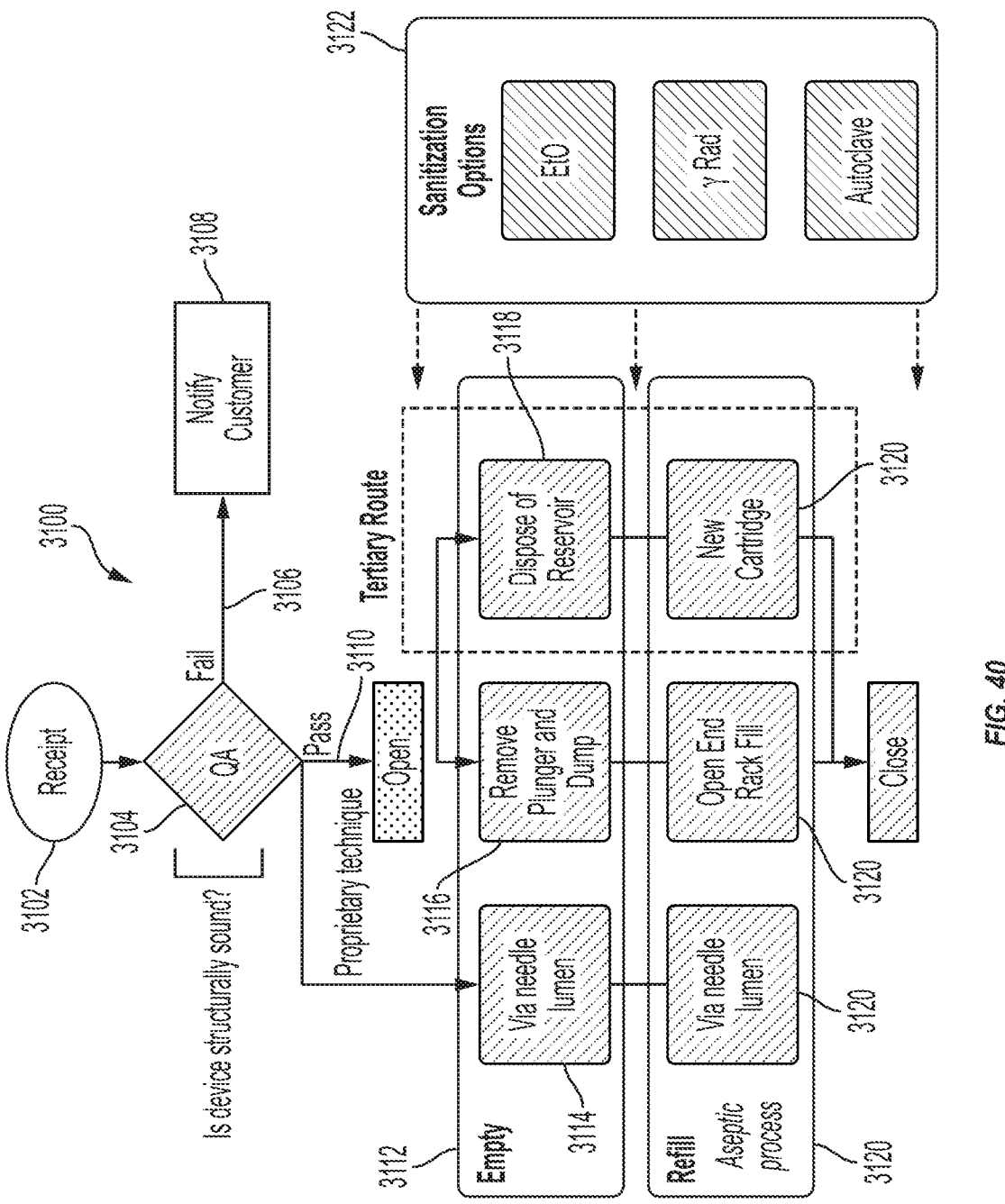

FIG. 40 is a flowchart illustrating various techniques for refilling medicament in an auto-injector, according to an embodiment of the present disclosure.

DETAILED DESCRIPTION

Definitions

Where the definition of terms departs from the commonly used meaning of the term, applicant intends to utilize the definitions provided below, unless specifically indicated.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/ or" unless stated otherwise. Furthermore, use of the term "including" as well as other forms, such as "include", "includes," and "included," is not limiting.

For purposes of the present disclosure, the term "comprising", the term "having", the term "including," and variations of these words are intended to be open-ended and mean that there may be additional elements other than the listed elements.

For purposes of the present disclosure, directional terms such as "top," "bottom," "upper," "lower," "above," "below," "left," "right," "horizontal," "vertical," "up,"

"down," etc., are used merely for convenience in describing the various embodiments of the present disclosure. The embodiments may be oriented in various ways. For example, the diagrams, apparatuses, etc., shown in the drawing figures may be flipped over, rotated by 90° in any direction, reversed, etc.

For purposes of the present disclosure, a value or property is "based" on a particular value, property, the satisfaction of a condition, or other factor, if that value is derived by performing a mathematical calculation or logical decision using that value, property or other factor.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present disclosure, the term "associated" with respect to data refers to data that are associated or linked to each other. For example, data relating the identity of an individual (identity data) wearing an integrated sensor module may be associated with the motion data for the individual obtained from an accelerometer or, optionally, from a gyroscope or, optionally, from the amplitude of the power signal from an energy harvester.

For the purposes of the present disclosure, the term "elastic deformation" refers to a temporary shape change that is self-reversing after the force is removed, so that the object returns to its original shape.

Description

While the disclosure is open to various modifications and alternative forms, specific embodiments thereof have been shown by way of example in the drawings and will be described in detail below. However, it should be understood that the disclosure is not intended to limit the disclosure to the particular forms disclosed, but on the contrary, the disclosure is to cover all modifications, equivalents, and alternatives falling within the spirit and the scope of the disclosure.

Disclosed embodiments provide a method and apparatus for opening auto-injectors for subsequent servicing and refilling with medicament. The disclosed apparatus will open and disassemble auto-injectors to gain access to its drug reservoir so that a replacement pharmaceutical may be applied. Disclosed embodiments provide for reassembling the auto-injector as a functional medical device. In some embodiments, the disclosed apparatus is configured to compress the outer body of the auto-injector such that at least a portion of the outer body is deformed enough for the actuation assembly to be released. In this manner, the elastic deformation allows a power pack (e.g., an actuation assembly) that seals the end of the auto-injector to slide out once the latching pins of the power pack clear the outer shell. In some disclosed embodiments, the exterior outer body comprises a malleable plastic shell of the auto-injector. After the shell is compressed, the power pack is removed by extending a mandrel through a hole in the power pack which serves as a safety/arming pin of the auto-injector. The mandrel is then expanded and grips the inside of the power pack (i.e., couples to the interior of the power pack) thereby creating enough traction and pulling force to slide the power pack from the shell for removal. In one disclosed embodiment, clamps may be utilized to grip the power pack from the outside in order to gain sufficient traction necessary to remove the power pack from the shell. Additionally, the clamps may be configured to fit latching pins to form a supplementary angle that facilitates both the compression and sliding of pins under the expanded shell.

A typical auto-injector has a housing which contains, for example, a drug reservoir which may be a cartridge. The cartridge has one or several chambers containing medicament compositions or components thereof and is adapted to be attached to a needle assembly. The cartridge can hold, for example, a pre-mixed liquid medicament or a solid medicament and a liquid that are mixed prior to injection. In some implementations, the cartridge may hold a plurality of liquids, or a plurality of solids, or combinations thereof. The housing carries an actuation assembly with a stored energy source, for example, a compressed spring. Activation of the actuation assembly causes a sequence of movements, whereby the needle extends from the auto-injector into the user so that the medicament compound is then forced through the needle and into the user. In some implementations, after delivery of the dose of medicament into the injection site the needle may remain in an extended position, whereas in alternative implementations, the needle may retract or otherwise be covered, e.g., by a shield. If the auto-injector is of the type designed to carry plural components of the medicament composition in separate, sealed compartments, structure may be included that forces the components to mix when the actuation assembly is activated.

One aspect of the present disclosure relates to an auto-injector for dispensing a predetermined dosage of a medicament. The medicament may be either self-administered or administered by a caregiver. The auto-injector includes a housing. The housing may comprise an oval or elliptical shape such that it is more ergonomic. The oval shape prevents the auto-injector from rolling off a table or flat surface, while providing a larger surface area for printing user instructions. A cartridge container is disposed within the housing. A cartridge is received within the cartridge container. The cartridge has at least one opening therein and contains a medicament. The medicament is rearwardly confined by a plunger. The cartridge includes a needle assembly to dispense the medicament there through. The cartridge is advanced within the cartridge container from a stored position to an operation position where the needle extends from the cartridge container such that the dose of medicament can be administered. An actuation assembly or power pack provides a stored energy source that is capable of being released to drive the plunger within the cartridge to dispense the medicament through the needle assembly into the user and allowing the needle to be accessible on activation.

Another aspect of the present disclosure is the construction and arrangement of the actuation assembly or power pack, which is mounted within the housing adjacent to an open end. A release pin or safe pin is removably attached to the actuation assembly to prevent inadvertent actuation of the auto-injector when the release pin is in place. A pin or stem on the release pin is received within an opening in the actuation assembly to prevent actuation of the auto-injector. This opening in the power pack (which may be described as an actuation assembly or actuator) is spaced from the open end of the housing such that the opening is less visible to a user prior to administering the drug. This arrangement is provided so that user will not orient the incorrect end of the auto-injector against the injection surface of the user. The power pack is recessed or spaced from the end of the housing, which provides an indication to the user that pressing the power pack will not operate the auto-injector. The recessed nature of the power pack serves to hide the release pin hole in the power pack when the user is viewing the instructions on the outer body such that the user does not confuse the release pin hole with the opening through which the needle passes for administering the medicament. The release pin may include at least one tab extending therefrom. The tab is compression fit into a complementary recess formed in the actuation assembly to prevent the inadvertent removal of the release pin. The tabs also prevent rotation of the release pin such that the user easily recognizes that the release pin must be pulled in order to be removed.

The actuation assembly includes an outer body, which is configured to engage the release pin. The outer body is constructed to be connected to the housing. An inner body is operatively coupled to the outer body. At least one retention tab on the inner body secures the inner body to the outer body. The inner body is capable of limited movement with respect to the outer body. A collet is operatively coupled to the inner body. An energy source is operatively connected to the inner body and the collet. In some disclosed embodiments, the collet may be molded as a single piece. No spacers or other components are provided between the collet and the plunger in the cartridge. This arrangement simplifies construction. Different sized collets can be produced and installed into the actuation assembly, such that only the collet needs to be altered when different sized cartridges are used or a different sized dosage of medicament is to be administered.

An exemplary auto-injector 100 will now be described in greater detail in connection with FIGS. 1-2 and 6-9. The auto-injector 100 includes an outer body 110, a release pin (a release pin assembly) 120, a power pack 130, a cartridge container 140, a needle cover 150 and a cartridge 160 housing a dose of medicament. The dose can be stored in liquid or solid form or as a combination of a liquid and a solid that is mixed prior to injection. In some embodiments, the dose may be stored as a combination of a plurality of liquids, a combination of a plurality of solids, or a combination of a plurality of liquids and solids.

The exemplary auto-injector 100 may include an outer body. The outer body 110 may include a generally oval or elliptical shape, which is more ergonomic sized to permit easy grasping and use by the user or caregiver in comparison with a cylindrical body. The generally oval shape of the outer body 110 prevents the auto-injector 100 from inadvertently rolling or sliding off a flat surface. Furthermore, the oval shape provides a larger print surface for labeling the auto-injector 100 with instructions. The outer body 110 is preferably formed from a synthetic material such that it can be easily molded. The outer body 110 can be transparent such that the interior components can be easily viewed through the outer body 110. With such a construction, the user can view the contents of the cartridge 160 through windows in the cartridge container 140 and the needle cover 150 at predetermined times. It is also contemplated that the outer body 110 can be opaque such that the interior components are not visible through the outer body 110. It is also contemplated that the outer body 110 has a window or windows that permit viewing of the components within the outer body 110. The outer body 110 has an opening 111 formed in one end that is sized to receive a release pin 120. When in place, the release pin 120 prevents inadvertent use or activation of the auto-injector 100.

Figures 3, 4, 5:
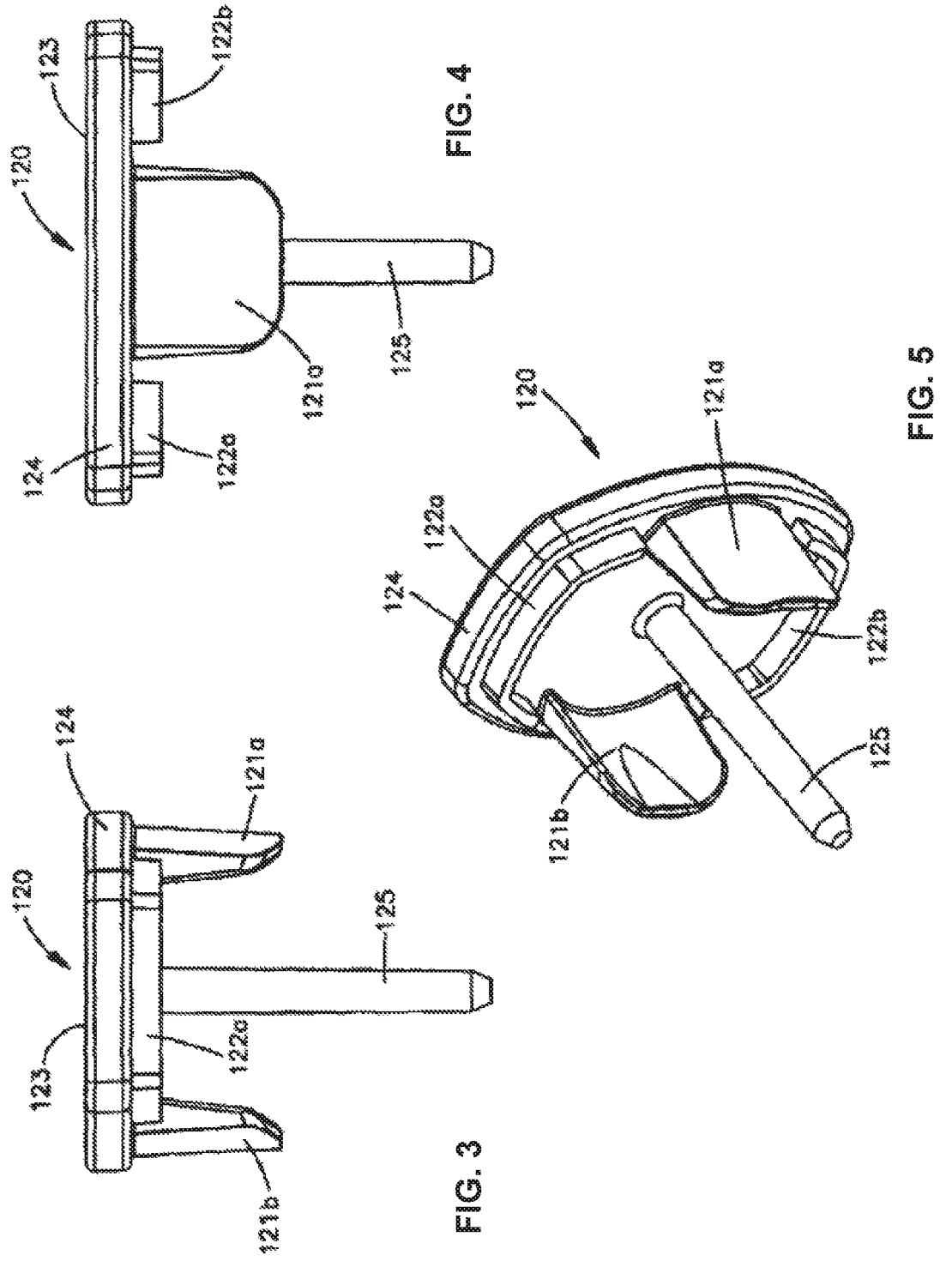
FIG. 3 is a side view of an exemplary release pin, according to an embodiment of the present disclosure.
FIG. 4 is another side view of the release pin of FIG. 3 rotated about an axis, according to an embodiment of the present disclosure.
FIG. 5 is a bottom perspective view of the safe release pin of FIG. 3, according to an embodiment of the present disclosure.
Figures 6, 7, 8, 9:
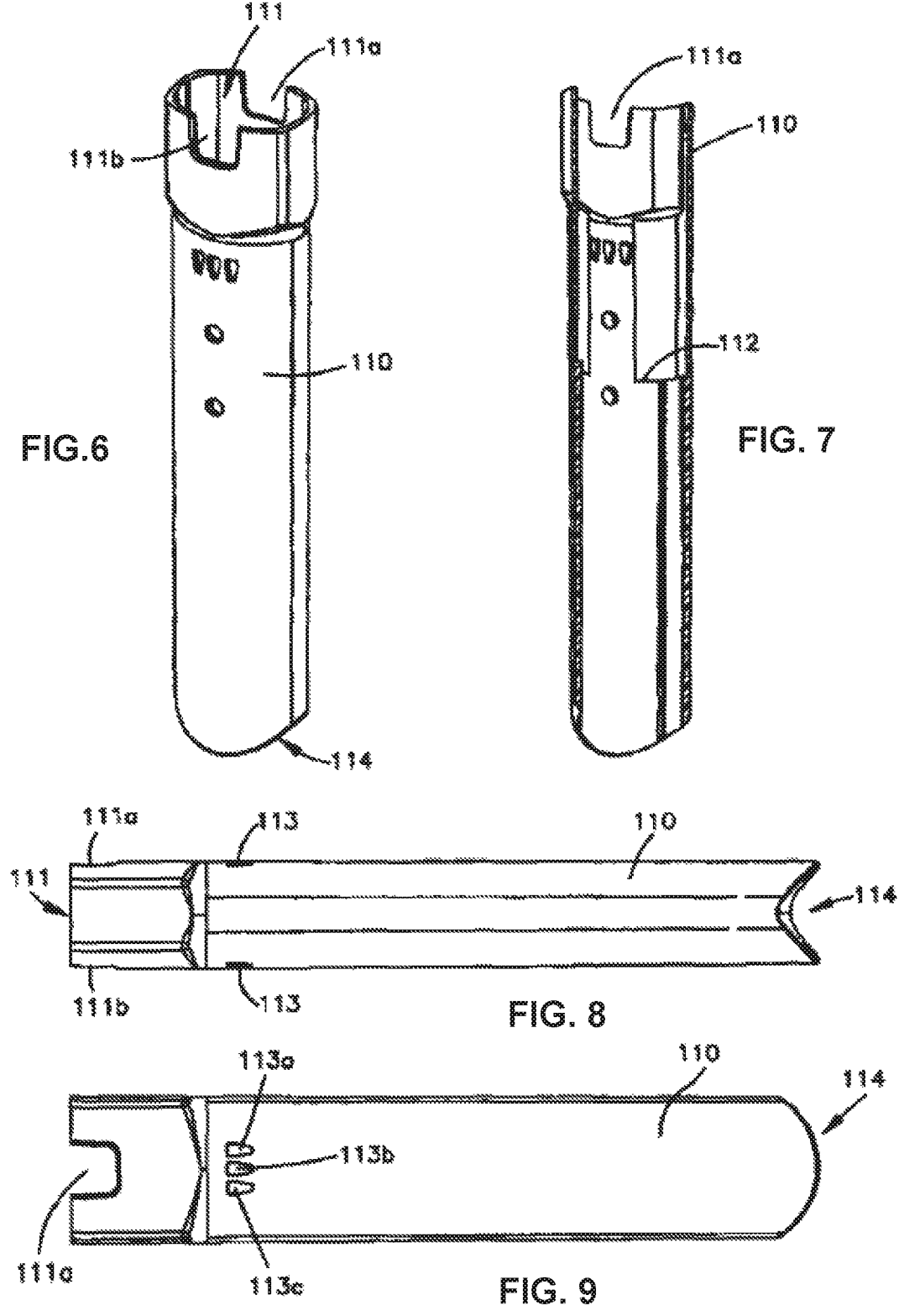
FIG. 6 is a left side perspective view of the exemplary outer body of the auto-injector, according to an embodiment of the present disclosure.
FIG. 7 is a partial cross sectional perspective view illustrating the interior of the exemplary outer body of the auto-injector, according to an embodiment of the present disclosure.
FIG. 8 is a side view of the outer body of the exemplary outer body of the auto-injector, according to an embodiment of the present disclosure.
FIG. 9 is another side view of the exemplary outer body of the auto-injector of FIG. 8 rotated 90 degrees about an axis, according to an embodiment of the present disclosure.

An exemplary detailed embodiment of the release pin 120 is illustrated in FIGS. 3-5. The release pin 120 may include downwardly projecting ribs 122a and 122b, which are adapted to be received on the top surface of the power pack 130. The ribs 122a and 122b increase the stability and rigidity of the release pin 120. It is contemplated that additional ribs may be provided. The release pin 120 may include an outwardly facing flat end 123 having a peripheral ledge 124. The peripheral ledge 124 permits grasping of the release pin 120 by the user. The ledge 124 is sized to rest on the end surface of the outer body 110 adjacent opening 111. The release pin 120 includes a downwardly extending pin 125, which engages the collet 430 of the power pack 130. When secured in place (i.e., prior to removal of the release pin 120 and prior to actuation of the auto-injector 100), the downwardly extending pin 125 prevents the end of the collet 430 from compressing, which prevents actuation of the auto-injector 100. The end 123 has a shape corresponding to the oval/elliptical shape of the outer body 110.

Turning to FIGS. 6-9, the opening 111 includes side recesses 111a and 111b, which extend downwardly along opposing sides of the outer body 110. While two recesses are shown, it is contemplated that a single recess may be provided or more than two may be provided. The number of recesses will correspond to the number of tabs. The recesses 111a and 111b are sized so that they may receive downwardly extending tabs 121a and 121b on the release pin 120. The tabs 121a and 121b prevent rotation of the release pin 120 such that the user easily recognizes that the release pin 120 is to be pulled rather than rotated to permit removal of the release pin 120 in order to actuate the auto-injector 100. The tabs 121a and 121b are primarily received in retention recesses 235 located on opposing sides of the power pack 130, described in greater detail below. The recesses 111a and 111b provide access to tabs 121a and 121b in the recesses 235. The tabs 121a and 121b are compression fit onto the power pack 130 to prevent inadvertent removal. To release the release pin 120, the operator compresses or pinches the tabs 121a and 121b to dislodge the edges of the tabs 121a and 121b from the recesses 235 such that the release pin 120 can then be pulled/removed from the power pack 130. As shown, the tabs 121a and 121b have a curvature which creates a chamfered edge that engages the edges of the recesses 235. The shape of the tabs 121a and 121b and the recesses 235 are fully complementary, which creates the friction or compressive retaining force between the pin 120 and power pack 130.

In an exemplary embodiment, the inner surface of the outer body 110 is contoured to receive the power pack 130, a cartridge container 140 and a needle cover therein 150. The needle cover 150 may be positioned between the container 140 and the outer body 110. Additionally, the mechanisms for locking and deploying the cover member may be located within the outer body 110 and are thus protected against tampering and contamination, such as dirt ingress. The outer body 110 includes a cartridge container retention step 112 formed on the inner surface near the end of the outer body 110 adjacent the opening 111. A ledge 142 of the cartridge container 140 abuts the retention step 112 to limit the downward movement of the cartridge container 140 within the outer body 110 once the auto-injector 100 has been assembled such that the container cannot be moved out of opening 114. A plurality of power pack retention openings 113a, 113b and 113c are formed on at least one side of the outer body 110. Projections or teeth 238 on the power pack 130 are snap fit into the openings 113. This snap fit prevents the removal of the power pack 130 from the outer body 110 once installed in the outer body 110. The power pack outer body 230 is not movable with respect to the outer body 110. The ledge 142 of the cartridge container 140 is sandwiched between the retention step 112 and the power pack 130.

An exemplary power pack 130 will now be described in greater detail in connection with FIGS. 10-18. The power pack 130 according to some embodiments may include structural components as described in U.S. Pat. No. 7,449,012 to Young et al. The power pack 130 may include a power pack outer body 230, a power pack inner body 330, a collet 430, and a power pack spring assembly 530. In one exemplary embodiment, the activation force necessary to release the energy stored in the power pack is between 4 to 8 pounds. The activation force is the force required to release the collet 430 from the inner body 330 when the auto-injector 100 is pressed against the injection surface. The injection force provided by the spring assembly 530 is approximately 30 pounds. The injection force must be sufficient such that the cartridge 160 is advanced within the cartridge container 140 to drive the needle such that it pierces the sheath to permit injection of the medicament into the user. The power pack outer body 230 is a generally cylindrical elongated hollow body 231. A plurality of outer peripheral ribs 232a, 232b and 232c shown in FIG. 11B extend outwardly from an outer surface of the hollow body 231. While these ribs 232 are shown, it is contemplated additional ribs may be provided. The ribs 232 are provided to prevent distortion of the outer body 110 of the auto-injector 100. A plurality of outer longitudinal ribs 233a, 233b is spaced about the outer surface of the hollow body 231. The ribs 233 cooperate with the ribs 232 to further strengthen the auto-injector 100 and prevent distortion of the outer body 110 when gripped and used by a user.

One of the peripheral ribs 232a forms a top end surface 237 of the power pack outer body 230. A hole 234 is provided in end surface which is sized to receive the downwardly extending pin 125 of the release pin 120. Retention recesses 235a and 235b are formed on opposing sides of the hollow body 231 adjacent the top end surface. The recesses 235a and 235b are formed by walls 236a and 236b which extend outwardly from the hollow body 231 and upwardly from the top end surface 237 of the peripheral rib 232a. The recesses 235a and 235b are aligned with the side recesses 111a and 111b of the outer body 110 such that when the release pin 120 is secured to the auto-injector 100, the tabs 121a and 121b are received in both recesses 235a and 235b. The recesses 235a and 235b are sized to apply a compressive force on the tabs 121a and 121b to secure the release pin 120 in place to prevent inadvertent removal.

A plurality of projections or teeth 238a, 238b, 238c is formed on the outer surface of the hollow body 231, as shown in FIG. 17. The teeth 238a, 238b, and 238c are sized to be snap fit into the openings 113a, 113b, and 113c, respectively, to secure the power pack 130 within the outer body 110. This construction permits these components 110 and 130 to be secured together without the need of an adhesive of other form of bonding. However, in some embodiments, a bond may be formed, e.g., with adhesive, and one or more of the teeth 238a, 238b, 238c and of the openings 113a, 113b, 113c may be omitted. A corresponding set of teeth may be provided or the opposite side of the hollow body 230 to match the corresponding openings in the outer body 110.

Figures 1, 2:
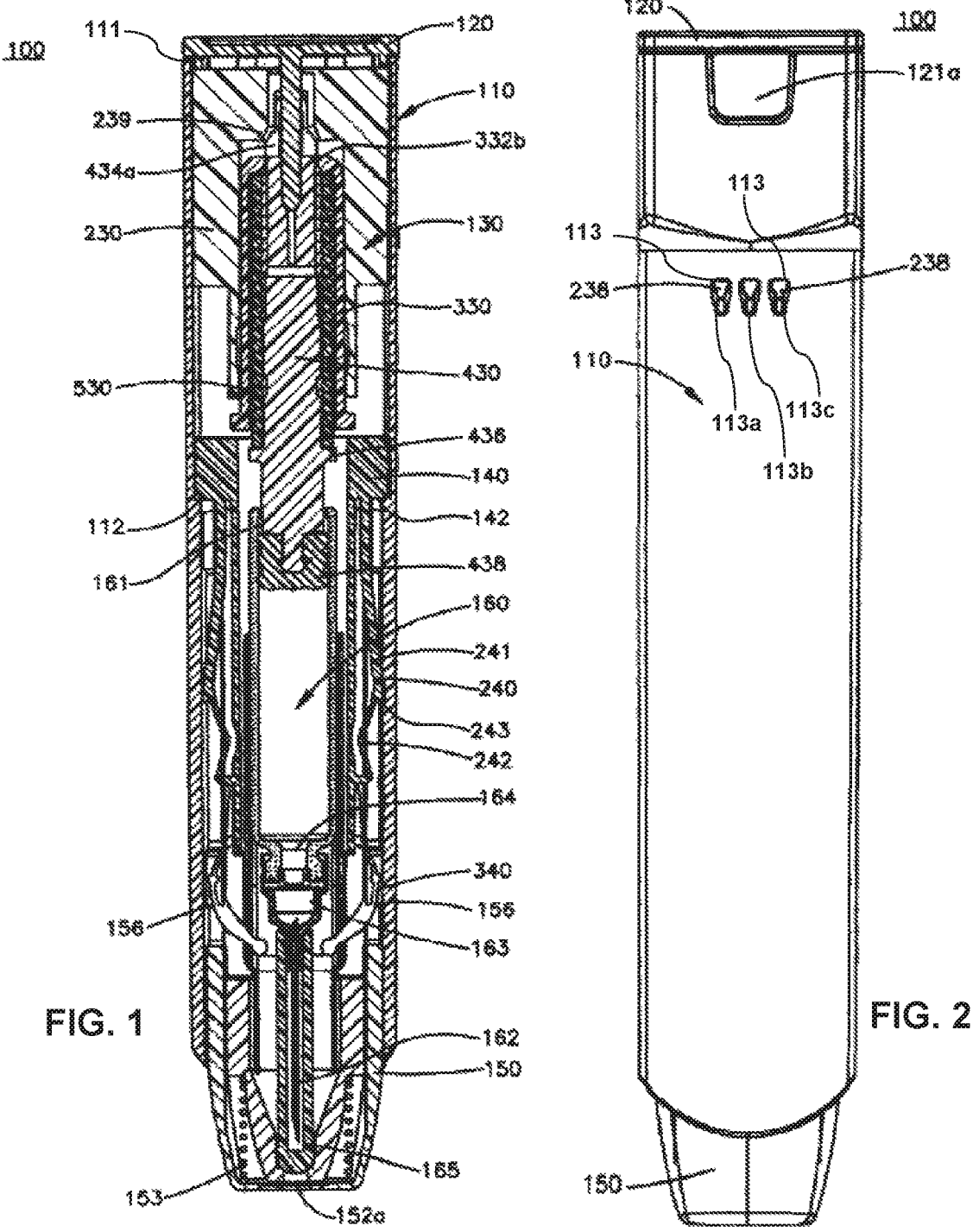
FIG. 1 is a side cross sectional view of an exemplary auto-injector, according to an embodiment of the present disclosure.
FIG. 2 is a side schematic view of the auto-injector in the unactivated state of FIG. 1, according to an embodiment of the present disclosure.

The interior of the hollow body 231 may include a recess 231a as shown in FIG. 11B, which is sized to receive a retention tab 334 (shown in FIG. 11B) on the power pack inner body 330. The recess 231a may be a groove, which extends about the inner periphery of the hollow body 231. The recess 231a is positioned in the hollow body 231 near an end opposite the end surface 237. As seen in FIGS. 1 and 10, a collet activation structure extends into the interior of the hollow body 231 from the inner side of the end surface 237. The collet activation structure has a generally cylindrical shape with a sloped collet activation surface located on a free end. The activation surface is provided such that when the pin 120 is removed and the front end of the injector is forced into an injection site so that cartridge container 140 rearwardly moves to engage inner body 330, this will rearwardly force tips of the collet 430 (described later) and particularly rearward surfaces thereof into engagement with activation surface to force the tips of the collet 430 together to release the spring assembly 530 and thus release the necessary energy to inject the medicament into the user. Ribs may be provided to reinforce the collet activation structure. It is contemplated that other means of releasing the collet 430 may be employed. A push button type actuation arrangement may be employed, which is described in greater detail in U.S. Pat. No. 4,031,893, which is incorporated by reference herein in its entirety for the background and techniques disclosed therein.

The power pack inner body 330 is a generally cylindrical hollow inner body 331. The hollow inner body 331 includes an opening 333 shown in FIG. 11A extending from a first end thereof to a second end thereof which is opposite to the first end. At the first end of the inner body 331, the opening has a collet assembly lead-in surface 332a as shown in FIG. 11D, which is used to compress a portion of the collet assembly 430 during assembly of the auto-injector 100 such that is can be properly mounted within the power pack inner body 330. As shown in FIG. 11C, the opening also has a collet retention surface 332b located on an external surface of the inner body 331, and the collet retention surface 332b supports the opposing tips (finial portions which may be shaped as arrowheads) 434a, 434b (shown in FIG. 15) of the collet 430 prior to activation. The opening of the hollow inner body 331 is positioned so as to be spaced from a plurality of retention tabs 334 which are sized to be snapped into the retention recess 231a. The recess 231 and tabs 334 permit limited movement between the power pack inner body 330 and the power pack outer body 230. The arrangement is also beneficial for purposes of assembling the auto-injector 100. The inner body 330 and the outer body 230 can be preassembled. The recess 231 and tabs 334 maintain the inner body 330 and the outer body 230 in proper alignment for assembly. Furthermore, this arrangement prevents the subassembly of the inner body 330 and the outer body 230 from separating prior to the final assembly in the auto-injector 100. It is also contemplated that other means which permit limited movement between outer and inner bodies of the power pack 130 (i.e., the actuation assembly), and which secure the components together, may be employed. A ledge 335 at least partially extends about the periphery of the opening. The ledge 335 is sized to engage the cartridge container 140 and the power pack outer body 230 at certain times during the operation of the auto-injector 100, described in greater detail below. A spacing exists between the inner power pack 330 and the cartridge container 140 after assembly and prior to activation of the auto-injector 100 to create a gap, which avoids permanently putting forces on the power pack and the spring 530.

A collet 430 as shown in FIG. 12 may be received within the hollow interior of the power pack inner body 330. In some disclosed embodiments, the collet 430 may be a molded one-piece construction. The collect 430 has an elongated body 431 having an opening 432 formed therein which forms a pair of side arms 433a and 433b. Each side arm 433a and 433b includes tips 434a and 434b (finial portions) respectively. One side of each tip 434a and 434b is configured to contact and engage the collet retention surface 332b. An opposite side of each tip 434a and 434b is configured to engage the collet assembly lead-in surface 332a, which permits the side arms 433a and 433b to be deflected inwardly to permit operation of the auto-injector 100. The end 435 of the collet 430 adjacent the tips 434a and 434b includes an opening 435a sized to receive the pin 125 of the release pin 120. The pin 125 prevents the side arms 433 from being deflected inwardly towards each other. When secured in place, the pin 125 prevents activation of the auto-injector 100.

The collet 430 is positioned within the power pack spring assembly 530. One end of the spring assembly 530 is supported on a flange 436 formed on the collet 430. The flange 436 extends outwardly from the elongated body 431. While the flange 436 supports one end of the spring assembly 530, the location of the flange 436 on the body 431 can also serve to define the delivered dose volume of medicament injected into the user. In certain applications it is desirable to control the amount of medicament delivered through the needle such that a portion of the medicament remains in cartridge 160. The flange 436 may limit the distance that the collet 430 can travel into the cartridge 160, which contains the liquid medicament. As such, the amount of medicament delivered is controlled. In this arrangement, the flange 436 is sized to contact the end of the cartridge 160. For larger diameter cartridges and for larger doses of medicament, it is contemplated that the flange 436 can travel within the cartridge 160. The collet 430 further includes a projection 437, which receives a plunger 438. The plunger 438 is slidably received within the cartridge 160. In other applications, it is desirable to dispense all of the medicament from the container 160. A small residual amount of medicament remains in the needle 162 and the neck of the cartridge 160 adjacent the needle 162. In these applications, the flange 436 travels within the interior of the cartridge 160 so that the plunger 438 travels the length of the interior of the cartridge 160 to dispense all of the medicament (except for the residual amounts mentioned above) through the needle 162. It is contemplated that different sized collets 430 may be used in the present auto-injector 100. As such, the collet 430 can be changed based upon cartridge size and desired dose.

The collet 430 may be formed as a single piece from a suitable plastic material. The one-piece collet 430 simplifies manufacturing and lowers costs by reducing the number of components needed to form a collet. In conventional collets, multiple brass components may be used. In addition, in other conventional auto-injectors, a spacer may be required for use in conjunction with the collet 430 to accommodate different amounts of medicament for different auto-injectors. The disclosed exemplary collet 430, however, eliminates the multi component construction and also advantageously eliminates the need for a spacer. The length of the collet can be selected based upon the desired dosage. This construction further permits the elimination of a metal insert typically found in the plunger and a firing seat above the power pack inner body. It is contemplated that the size and shape of the collet 430 itself may be varied to accommodate different sized cartridges 160. When the flange 436 does not contact the cartridge 160, it is possible to dispense the entire contents of the cartridge 160 except for any residual amounts remaining in the needle or in the neck of the cartridge 160. It is contemplated that a nipple plunger, as disclosed in U.S. Pat. No. 5,713,866 to Wilmot, the entire disclosure of which is incorporated herein by reference for the background and techniques disclosed therein, may be employed prevent any buildup of residual amounts of medicament in the neck of the cartridge 160. The position of the flange 436 can be varied to control the amount of dosage injected into the user when the flange is positioned such that the collet and the plunger 438 travel a greater distance within the cartridge 160 before the flange 436 contacts the cartridge 160, a larger dose is dispensed. The length of the collet 430 and the diameter of the cartridge 160 can be selected to control the flow of fluid through the needle 162 of the cartridge 160 so that a desired flow rate is obtained. The auto-injector 100 in accordance with one or more embodiments is configured such that collets 430 of varying sizes can be used within the same outer body 110 and the power pack 430.

An opposite end of the spring assembly 530 rests against an inner surface of the power pack inner body 330 against the opening.

In general, auto-injectors are constructed to be tamper proof and resistant to damage while also being intended for disposal after use or expiry. Being able to open and reassemble an auto-injector will allow it to be serviced or refilled with medicament instead of necessitating the disposal of the auto-injector. The apparatus of one or more embodiments can service auto-injectors by opening/disassembling them in a manner to be serviced and reassembled so that the auto-injector can be refilled and reliably used.

Turning now to FIGS. 19-29, an embodiment of the disclosed tool or apparatus 1900 for servicing an exemplary auto-injector 100 is illustrated. Components of apparatus 1900 may be disposed/affixed on a service table (a base or support base) 1902. Service table 1902 may include stabilizing feet 1904 to provide stability and function as anti-friction stop surfaces to service table 1902. Stabilizing feet 1904 may be affixed to an undersurface of service table 1902 by one of a variety of retaining fixtures including, for example, threaded fasteners 1906 and/or alternatively, adhesives, hook and fastener materials or any other structure sufficient to retain stabilizing feet 1904 at prescribed locations along service table 1902.

Additional components secured to a top side 1908 of service table 1902 include an end stop 2102, hold down cavity 1912 (i.e., a receiver), restraining and device deforming clamp assembly 1914, and extractor handle assembly 1916. As illustrated in FIG. 20, a bottom view 2000 of apparatus 1900 illustrates that each of the end stop 2102, hold down cavity 1912, restraining and device deforming clamp assembly 1914, and extractor handle assembly 1916 may be affixed to service table 1902 by one of a variety of retaining fixtures including, for example, threaded fasteners 2002, secured through the underside 2004 of service table 1902. Slots 2006 may be provided in the service table 1902 to allow for adjustability and multi-positioning of end stop 2102 and extractor handle assembly 1916. Such adjustability and multi-positioning may accommodate various lengths of auto-injectors 100 and an ability to more precisely control applied extraction forces from extractor handle assembly 1916.

In at least one embodiment, hold down cavity 1912 as shown in FIG. 23 is a receiver that accommodates auto-injector 100 disposed within a cavity 1910 designed to generally receive a portion of outer body 110 of auto-injector 100. Hold down cavity 1912 may also include an interchangeable cavity insert 1918 as shown in FIG. 22.

Interchangeable cavity insert 1918 is designed to take up slack and allow for outer body 110 expansion, for example, generally in a deformation area 1920 of outer body 110. In some disclosed embodiments, interchangeable cavity insert 1918 may include a different material from hold down cavity 1912 to accommodate flexible outer body 110 deformation, for example, during a retaining, deformation and/or compression operation, as described below. In some embodiments, the interchangeable insert 1918 may be incorporated into the receiver 1912.

Restraining and device deforming clamp assembly 1914 includes hold down clamp die (clamp) 1922. Hold down clamp die 1922 is mechanically coupled (such as via a series of pins, pivots and levers) to a restraining and deforming handle 1924. Movement of hold down clamp die 1922 may be actuated by enactment of restraining and deforming handle 1924 from a first position to a second position and vice versa. When restraining and deforming handle 1924 is placed in the first position, hold down clamp die 1922 may simultaneously be actuated to achieve a non-clamped position in a non-clamped state. When restraining and deforming handle 1924 is placed in the second position, hold down clamp die 1922 may simultaneously be actuated to achieve a clamped position in a clamped state.

In one disclosed embodiment, restraining and deforming handle 1924 is attached to a base 1926 of restraining and device deforming clamp assembly 1914 shown in FIG. 25. Restraining and deforming handle 1924 may include a handle support bracket 1928 pivotably attached to a base support brackets 1932 such as via pins. Base support brackets 1932 are secured to base 1926 such as via fastening members 1934. One end 2104 of a lever 1936 may also be pivotably attached to base support brackets 1932 such as via pin assembly 1930. A press support 1938 may be disposed and pivotably attached between handle support brackets 1928. A position of press support 1938 may also include being disposed above a contact surface 1940 of lever 1936. Another end 1942 of lever 1936 may be attached to hold down clamp die 1922. In one disclosed embodiment, hold down clamp die 1922 is engaged with end 1942 of lever 1936 via a threaded fastener assembly 1944. Threaded fastener assembly 1944 may comprise a threaded fastener 1946 extending from hold down clamp die 1922 through end 1942 and secured thereto via a corresponding threaded nut 1948. In some select embodiments, a threaded nut 1948 may be disposed along threaded fastener 1946 above and below hold down clamp die 1922. Threaded fastener assembly 1944 allows for adjustment and manipulation of hold down clamp die 1922 which may also include an ability of adjusting an applied clamping force. In at least one embodiment, restraining and deforming handle 1924 moves to urge hold down clamp die 1922 toward the receiver and the seated auto-injector 100. For example, in some embodiments, the restraining and deforming handle 1924 moves to urge hold down clamp 1922 toward the auto-injector (e.g., in a direction generally perpendicular to a longitudinal axis of auto-injector 100). However, it is contemplated that other designs may be employed. For example, such designs may include a configuration wherein restraining and deforming handle 1924 operates in a different direction such as parallel to the seated longitudinal axis of auto-injector 100 and/or in tandem with clamp handle 1952 and/or extractor handle assembly 1916.

In operation, a forward rotational movement about the long axis of service table 1902 enables press support 1938 to abut contact surface 1940 thereby urging lever 1936 generally downwardly. The downward motion is translated to hold down camp die 1922 to achieve a pressing operation, for example, against an outer body 110 of an auto-injector 100 disposed within hold down cavity 1912, as explained below.

Extractor handle assembly 1916 comprises a base portion 1950 to which an extractor clamp handle 1952 is pivotably attached such as by pin assembly 1954. A linkage assembly 1956 is configured to couple a shaft extension 1958 at one end 1960 to a bracket support 1962 of extractor clamp handle 1952 such as via pin assembly 1964. The other end 1966 of shaft extension 1958 may be coupled to an extractor clamp assembly 1968. In some embodiments, the extractor handle assembly 1916 and extractor clamp assembly 1968 serve as an extractor to facilitate removal of the power pack 130 from the auto-injector 100.

Extractor clamp assembly 1968 may comprise complementary clamping members 2108, 2110 pivotally connected to a support bracket assembly, as seen in FIG. 26. The support bracket assembly may comprise a bottom support bracket 2118 and a top support bracket 2140. Clamping members 2108, 2110 may be connected to support bracket assembly via fastener or pin assemblies 2124. In one disclosed embodiment, a cam assembly 2958 may be employed to pivot forward ends 2126, 2128 of complementary clamping members 2108, 2110, respectively, together. Such motion may clamp together forward ends 2126, 2128 to sides of outer body 110, as described below. Cam assembly 2958 may be engaged by rotating cam knob 2138. As illustrated, for example, in FIGS. 21, 27 and 29, each of complementary clamping members 2108, 2110 may be coupled to shaft extension 1958 via shaft coupling assembly 2130. In one embodiment shaft extension 1958 may be internally threaded to receive a mating threaded fastener 2950. Thus an end 2750 of shaft extension 1958 may be placed in abutment with collar 2952 of shaft coupling assembly 2130. Threaded fastener 2950 is inserted through a receiving hole 2752 in collar 2952 and into a complementary threaded receptacle 2754 of shaft extension 1958 thereby retaining shaft coupling assembly 2130 to shaft extension 1958. Cam knob 2138 may be coupled to cam portion 2756 such as via fastener 2758 to induce rotation as described below.

FIG. 29 illustrates extractor clamp assembly 1968 having the top support bracket 2140 and cam knob 2138 removed. A biasing member 2956, such as an elastic member, or O-ring, or spring, is coupled to each of clamping members 2108, 2110 such as via fasteners 2972. A cam assembly 2958 is disposed between clamping members 2108, 2110. In a select embodiment, cam assembly 2958 may comprise a cam design having generally oval configuration with two elongated end points 2960, 2962 along a first axis which are generally longer than two shorter end points 2964, 2966 along a second axis wherein the second axis is generally perpendicular to the aforementioned first axis. When rotated, the longer end points 2960, 2962 may contact interior contact surfaces 2968, 2970 of clamping members 2108, 2110, respectively. This causes forward ends 2126, 2128 of complementary clamping members 2108, 2110, respectively, to pivot toward one another. Continual rotation of cam assembly 2958 disengages longer end points 2960, 2962 from contacting contact surfaces 2968, 2970 where upon biasing member 2956 compress and rotate forward ends 2126, 2128 away from one another.

Bottom support bracket 2118 may comprise a linkage member 2974 extending, for example, generally toward the top support bracket 2140. A safety pin 2976 may be configured to extend from linkage member 2974. In a disclosed embodiment safety pin 2976 is rigidly secured to linkage member 2974, such as by threaded connectors.

Turning to FIG. 37, removal of the power pack 130 from auto-injector 100 in accordance with disclosed embodiments requires removal of release pin 120 from outer body 110. Release pin 120 is removed from an end opening 111 of auto-injector 100. The recesses 111a (not shown) and 111b provide access to downwardly extending tabs 121a and 121b, respectively, of release pin 120. The tabs 121a and 121b are primarily received in retention recesses 235 (not shown) located on opposing sides of the power pack 130. As described earlier, hole 234 is provided in an end surface of the power pack 130 which is sized to receive the downwardly extending pin 125 of the release pin 120.

Auto-injector 100 is now prepared for removing its internal power pack 130 via apparatus 1900. The prepared auto-injector 100 is disposed within cavity 1910. A bottom end 2136 is abutted against end stop 2102 for support. Handle 1924 may be pulled forward to position hold down clamp die 1922 against outer body 110. Abutting pressure caused by hold down clamp die 1922 steadily holds down auto-injector 100 and slightly deforms outer body 110. The elastic deformation of outer body 110 caused by hold down clamp die 1922 facilitates dislodgement of projections or teeth 238 on the power pack 130 from openings 113. Once dislodged, power pack 130 may be removed from outer body 110.

Extractor handle assembly 1916 is enabled by lowering extractor clamp handle 1952 wherein extractor clamp assembly 1968 urged towards auto-injector 100 as a coupling device that couples to the auto-injector 100. Safety pin 2976 is aligned with and inserted into hole 234 of auto-injector 100. Disclosed embodiments provide this design feature in order to maintain the safety of the auto-injector 100 components such as preventing undesirable deployment of the needle. Forward ends 2126, 2128 are clamped to side recesses 111a and 111b of outer body 110 by rotating cam knob 2138 to cause end points 2960, 2962 to contact interior contact surfaces 2968, 2970, respectively. Once positioned and assembled, extractor clamp handle 1952 of extractor handle assembly 1916 is pulled in a direction away from auto-injector 100. The clamping force of forward ends 2126, 2128 is sufficient to grip side recesses 111a and 111b of outer body 110 for dislodging power pack 130 from auto-injector 100. To dislodge power pack 130 from auto-injector 100, extractor clamp handle 1952 is pulled away from auto-injector 100. This motion causes shaft extension 1958 coupled to extractor clamp assembly 1968 to move axially away from auto-injector 100, thereby retracting the clamped power pack 130 from outer body 110. Once power pack 130 is removed from auto-injector 100, safety pin 2976 may also be removed from hole 234.

FIGS. 29-34 illustrate another embodiment of the disclosed apparatus 1900 wherein a mandrel 3402 is introduced within the extractor clamp assembly 1968 as an exemplary coupling device. In this disclosed embodiment, a mandrel 2116 is configured to be disposed between extended forward portions 2120, 2122 of complementary clamping members 2108, 2110, respectively. In a select design, an extension 3404 is coupled to linkage member 2974 extending generally perpendicular to assembled complementary clamping members 2108, 2110. Extension 3404 is connected to mandrel 2116 such that as shaft extension 1958 is withdrawn and extended, mandrel 2116 moves accordingly.

FIGS. 35-36 detail additional features of a mandrel safety pin assembly 2600 utilized by the apparatus 1900. Mandrel safety pin assembly 2600 may include mandrel safety cap 2606. Mandrel safety cap 2606 is dimensioned and sized to fit opening 111 of outer body 110. It is designed to orient components of auto-injector 100 during the disclosed disassembly procedure. Additional features of mandrel safety cap 2606 may include designing its exterior side surface outer walls 2626 to be flush with the exterior outer walls of outer body 110. One or more flanges 2628 may be configured to extend away from underside 2610, such as, along an inside perimeter of exterior side surface outer walls 2626. In one disclosed embodiment, the positioning of flanges 2628 is configured to position and generally abut its exterior wall 2628 against the interior wall of outer body 110 when expanding mandrel safety cap 2606 is inserted within opening 111. The positioning and size dimensions of flanges 2628 provide structural support from within the interior of auto-injector 100 walls. At the same time, the positioning and size dimensions of flanges 2628 may be configured such that exterior side surface outer walls 2626 remain flush with exterior outer walls of outer body 110 during assembly.

An expansion flexure assembly 2608 is configured to extend away from an underside 2610 of expanding mandrel safety cap 2606. Expansion flexure assembly 2608 may comprise a plurality of expansion flexures 2614 arranged, for example, in a circular configuration about a hollow diameter. In one disclosed embodiment, the plurality of expansion flexures 2614 may be configured to extend from an underside 2610 of expanding mandrel safety cap 2606 in a first circular configuration 2618 having a first exterior diameter. End portions 2620 of the plurality of expansion flexures 2614 extending away from underside 2610 may terminate to form a second circular configuration 2622 having a second exterior diameter different than the first diameter. In an exemplary embodiment, the second exterior diameter is larger than the first exterior diameter. Consequently, a top surface or flanged area 2624 is radially formed by the expanded exterior diameter of the second circular configuration 2622 of the plurality of expansion flexures 2614.

A mandrel safety pin 2612 extends through the center of the hollow diameter of the plurality expansion flexures 2614. Mandel safety pin 2612 is provided as a safety precaution feature to replace pin 125 of release pin 120 to prevent unwanted dislodging of the needle in auto-injector 100. Mandrel safety pin 2612 is configured to move axially and independently within the hollow diameter formed by the plurality of expansion flexures 2614 as indicated by the directional arrows. In one disclosed embodiment, mandrel safety pin 2612 is integrally connected to coupling member 2604 such that mandrel safety pin 2612 is inserted through an internal bore of mandrel 2116, expanding mandrel safety cap 2606 and expansion flexure assembly 2608. In one disclosed embodiment, a portion 2616 of the diameter of mandrel safety pin 2612 may be configured to a greater external diameter dimension than the internal diameter of the hollow diameter formed by the circular configuration 2618 of the plurality of expansion flexures 2614. Thus, as the portion 2616 having the greater external diameter dimension moves axially within the internal hollow diameter, portion 2616 expands the plurality of expansion flexures 2614 upon contact. Consequently, the flanged area 2624 is also deflected to radially expand and increase.

Turning to FIG. 37, as described earlier, removal of the power pack 130 from auto-injector 100 in accordance with disclosed embodiments requires removal of release pin 120 from outer body 110. Release pin 120 is removed from an end opening 111 of auto-injector 100. The recesses 111a (not shown) and 111b provide access to downwardly extending tabs 121a and 121b, respectively, of release pin 120. The tabs 121a and 121b are primarily received in retention recesses 235 (not shown) located on opposing sides of the power pack 130. As described earlier, hole 234 is provided in an end surface of the power pack 130 which is sized to receive the downwardly extending pin 125 of the release pin 120.

In accordance with the described alternate embodiment, in operation, expanding mandrel safety cap 2606 is designed to replace existing safety release pin 120. FIG. 38 illustrates a cut-away view 2900 of the expanding mandrel safety pin assembly 2600 in connection with the power pack 130 of auto-injector 100, according to an embodiment of the present disclosure. As shown in FIG. 38, removed safety release pin 120 is replaced with expanding mandrel safety cap 2606 at end opening 111 of auto-injector 100. The expanding mandrel safety pin assembly 2600 is attached to the power pack 130 assembly by inserting expansion flexure assembly 2608 comprising the plurality of expansion flexures 2614 through hole 234. Once expansion flexures 2614 have breached through the interior top 2902 of power pack 130 through hole 234, mandrel safety pin 2612 is inserted axially through expansion flexure assembly 2608. Due to the greater external diameter of portion 2616, retracting mandrel safety pin 2612 through expansion flexure assembly 2608 causes the plurality of expansion flexures 2614 to expand and to be deflected radially outwardly thereby creating a larger diameter of the exterior circumference 2904 of expansion flexure assembly 2608 than the interior diameter of hole 234 of power pack 130. The auto injector 100 may then be prepared for removal of its internal power pack 130 as described above.

Extractor handle assembly 1916 is enabled by lowering extractor clamp handle 1952 to latch expanding mandrel safety cap 2606. Expanding mandrel safety pin assembly 2600 is attached to extractor clamp assembly 1968, such as via support bracket 2118. Forward ends 2126, 2128 are clamped to side recesses 111a and 111b of outer body 110. Once positioned and assembled, extractor clamp handle 1952 of extractor handle assembly 1916 is pulled in a direction away from auto-injector 100 to dislodge power pack 130 from auto-injector 100. During the dislodging step, expansion flexure assembly 2608 is withdrawn to be dislodged from within hole 234 through an opposite movement/direction from which it was inserted. As described above, retraction of the inserted mandrel safety pin 2612 through expansion flexure assembly 2608 causes the plurality of expansion flexures 2614 to expand and to be deflected radially outwardly thereby creating a larger diameter of the exterior circumference 2904 of expansion flexure assembly 2608 than the interior diameter of hole 234 of power pack 130. In some disclosed embodiments, mandrel safety pin 2612 may be configured as a chamfered/angled mandrel that engages the plurality of expansion flexures 2614 to expand when insert through the expansion flexure assembly 2608. Withdrawal of expansion flexure assembly 2608 from within hole 234 causes contact surfaces 2906 of the expanded plurality of expansion flexures 2614 to abut interior top 2902 of power pack 130. The materials and design of the expanded plurality of expansion flexures 2614 are sufficiently strong to engage, support pulling and dislodging power pack 130 and spring assembly 530 from outer body 110 of auto-injector 130 when sufficient withdrawal force is applied by extractor handle assembly 1916. A needle may be attached to a drug reservoir, for example, which is attached via vacuum to a rubber plunger head that comes out with the power pack 130.

FIG. 39 illustrates an exemplary power pack 130 removed from the auto-injector body by the disclosed apparatus 1900 wherein release pin 120 has been reinserted into opening 111. Once power pack 130 is removed, auto-injector 100 may be serviced. For example, servicing may include replacing and/or refilling of the cartridge of auto-injector 100 with medicament. After refilling, power pack 130 may be reinserted within outer body 110 of auto-injector 100, for example, in accordance with the embodiments described herein. Thus, reinstallation of power pack 130 may include urging projections or teeth 238 on the power pack 130 to snap fit into openings 113 as described earlier. The snap fit prevents the removal of the power pack 130 from the outer body 110 once installed in the outer body 110. Once inserted, the power pack outer body 230 is not movable with respect to the outer body 110.

Exemplary servicing techniques 3100 for refilling medicament in auto-injector 100 are presented in the flowchart of FIG. 40. In one disclosed embodiment, an auto-injector 100 is presented and received for servicing 3102. An initial inspection 3104 of auto-injector 100 may occur to determine if it is structurally sound and/or serviceable. If a determination is made that auto-injector 100 is not serviceable 3106, a user is notified 3108 and servicing of the auto-injector 100 is rejected. If a determination is made that auto-injector 100 is serviceable 3110, an exemplary technique may be employed, for example, for refilling auto-injector 100.

To begin, power pack 130 of auto-injector 100 is removed by the disclosed apparatus 1900. In some embodiments, once the power pack 130 is removed, one or more remaining components of the auto-injector 100 may be retained within the apparatus 1900. A service technician is presented with options for emptying any remaining medicament 3112 from auto-injector 100. Removal of the same may occur via needle lumen 3114, removing the internal plunger and disposing of any remaining medicament 3116 or disposing of the cartridge. Refilling techniques 3120 may be based upon the specific emptying technique 3112 employed by the service technician. For example, based upon removal of medicament via needle lumen 3114, medicament may also be refilled by needle lumen 3120. Based upon removal of medicament by removing the internal plunger and dumping any remaining medicament 3116, medicament may be refilled by rack filling auto-injector 100 through the open end 3120. Based upon removal of medicament by disposing of the reservoir 3118, medicament may be refilled by obtaining a new or refilled medicament cartridge 3120. Given the technique for disposing of the reservoir 3118 and refilling auto-injector 100 with a new or refilled medicament cartridge 3120, additional servicing operations may be employed and/or necessary. Such options may include employing prescribed sanitization options 3122 to ensure safety and health standards for medical distribution. Once auto-injector 100 is refilled with medicament, power pack 130 is reinserted into auto-injector 100 and closed for updated and continued use.

Having described the many embodiments of the present disclosure in detail, it will be apparent that modifications and variations are possible without departing from the scope of the disclosure defined in the appended claims. Furthermore, it should be appreciated that all examples in the present disclosure, while illustrating many embodiments of the disclosure, are provided as non-limiting examples and are, therefore, not to be taken as limiting the various aspects so illustrated.

All documents, patents, journal articles and other materials cited in the present application are incorporated herein by reference.

What is claimed is:

1. A system for servicing an auto-injector, the system comprising:

the auto-injector having an outer body; and an apparatus for servicing the auto-injector, comprising:

a base;

a receiver coupled to the base and configured to accommodate the auto-injector therein;

a clamp assembly coupled to the base and configured to move from a first position in which the clamp assembly is in a non-clamped state to a second position in which the clamp assembly is in a clamped state, the clamp assembly comprising a clamp die, and an actuator assembly including a lever mechanically coupled to the clamp die, wherein when engaged, the actuator assembly is configured to control the clamp die to move to restrain the auto-injector and to further control the clamp die to move to compress and deform the outer body of the auto-injector causing a temporary shape change of the of the outer body of the auto-injector until the deformation of the outer body of the auto-injector causes release of an actuation assembly from the outer body of the auto-injector; and an extractor coupled to the base and including a coupling device structured to couple to the actuation assembly of the auto-injector, the extractor being configured to be moved in a direction away from the auto-injector to cause the coupling device to pull the actuation assembly out of the auto-injector.

2. The system of claim 1, wherein the extractor comprises a mandrel assembly including:

a mandrel pin being configured to prevent movement of a needle of the auto-injector.

3. The system of claim 1, wherein the receiver includes an insert disposed at one end of the receiver and configured to receive a portion of the outer body of the auto-injector.

4. The system of claim 1, wherein the clamp assembly is configured to exert force on the auto-injector and cause release of the actuation assembly from the outer body of the auto-injector.

5. The system of claim 4, wherein the force exerted on the auto-injector by the clamp assembly causes projections on the actuation assembly to disengage from corresponding openings on the outer body of the auto-injector so as to release the actuation assembly from the outer body.

* * * * *